United States Patent
Assefa et al.

(10) Patent No.: US 9,481,639 B2
(45) Date of Patent: *Nov. 1, 2016

(54) SUBSTITUTED TETRACYCLINE COMPOUNDS FOR TREATMENT OF INFLAMMATORY SKIN DISORDERS

(71) Applicant: Paratek Pharmaceuticals, Inc., Boston, MA (US)

(72) Inventors: Haregewein Assefa, Braintree, MA (US); Beena Bhatia, Mansfield, MA (US); Michael P. Draper, Windham, NH (US); Laura Honeyman, Etobicoke (CA); Oak K. Kim, Cambridge, MA (US); Dennis P. Molnar, Hopkinton, MA (US)

(73) Assignee: Paratek Pharmaceuticals, Inc., Boston, MA (US)

(*) Notice: Subject to any disclaimer, the term of this patent is extended or adjusted under 35 U.S.C. 154(b) by 233 days.

This patent is subject to a terminal disclaimer.

(21) Appl. No.: 13/987,655

(22) Filed: Aug. 19, 2013

(65) Prior Publication Data

US 2013/0345179 A1    Dec. 26, 2013

Related U.S. Application Data

(63) Continuation of application No. 11/963,509, filed on Dec. 21, 2007, now Pat. No. 8,513,223.

(60) Provisional application No. 60/876,434, filed on Dec. 21, 2006.

(51) Int. Cl.
   *C07C 237/48* (2006.01)
   *A61K 31/65* (2006.01)
   *C07C 237/26* (2006.01)

(52) U.S. Cl.
   CPC .......... *C07C 237/48* (2013.01); *A61K 31/65* (2013.01); *C07C 237/26* (2013.01); *C07C 2103/46* (2013.01)

(58) Field of Classification Search
   CPC .. A61K 31/65; C07C 237/26; C07C 237/48; C07C 2103/46
   USPC ........................................................ 514/152
   See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,165,531 A | 1/1965 | Nelson et al. | |
| 3,304,227 A | 2/1967 | Loveless | |
| 3,454,697 A | 7/1969 | Joyner et al. | |
| 3,557,280 A | 1/1971 | Weber et al. | |
| 3,674,859 A | 7/1972 | Beutel et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 4,666,897 A | 5/1987 | Golub et al. | |
| 4,704,383 A | 11/1987 | McNamara et al. | |
| 4,806,372 A | 2/1989 | Strumskis | |
| 4,925,833 A | 5/1990 | McNamara et al. | |
| 4,935,412 A | 6/1990 | McNamara et al. | |
| 5,021,407 A | 6/1991 | Levy | |
| 5,231,017 A | 7/1993 | Lantero et al. | |
| 5,258,371 A | 11/1993 | Golub et al. | |
| 5,258,372 A | 11/1993 | Levy | |
| 5,308,839 A | 5/1994 | Golub et al. | |
| 5,321,017 A | 6/1994 | Golub et al. | |
| RE34,656 E | 7/1994 | Golub et al. | |
| 5,459,135 A | 10/1995 | Golub et al. | |
| 5,523,297 A | 6/1996 | Pruzanski et al. | |
| 5,532,227 A | 7/1996 | Golub et al. | |
| 5,589,470 A | 12/1996 | Levy | |
| 5,668,122 A | 9/1997 | Fife et al. | |
| 5,770,588 A | 6/1998 | McNamara et al. | |
| 5,773,430 A | 6/1998 | Simon et al. | |
| 5,789,395 A | 8/1998 | Amin et al. | |
| 5,811,412 A | 9/1998 | Levy | |
| 5,827,840 A | 10/1998 | Ramamurthy et al. | |
| 5,834,449 A | 11/1998 | Thompson et al. | |
| 5,834,450 A | 11/1998 | Su | |
| 5,837,696 A | 11/1998 | Golub et al. | |
| 5,843,925 A | 12/1998 | Backer et al. | |
| 5,919,774 A | 7/1999 | Bach et al. | |
| 5,919,775 A | 7/1999 | Amin et al. | |
| 5,929,055 A | 7/1999 | Ryan et al. | |
| 5,977,091 A | 11/1999 | Nieman et al. | |

(Continued)

FOREIGN PATENT DOCUMENTS

| | | | |
|---|---|---|---|
| DE | 2346535 A1 | 4/1974 | |
| FR | 2208885 A1 | 6/1974 | |

(Continued)

OTHER PUBLICATIONS

McCoy, K. Rosacea. The Merck Manual (2008), accessed online at http://www.merckmanuals.com/professional/print/sec10/ch111/ch111d.html.

Xie et al., "Squaric Acids: A New Motif for Designing Inhibitors of Protein Tyrosine Phosphatases", Organic Letters, 6(1):83-86 (2004).

Berge et al., "Pharmaceutical Salts", J. Pharm. Sci., 66(1):1-19 (1977).

Nilges et al., "Identification and Characterization of a Tetracycline Semiquinone Formed during the Oxidation of Minocycline", J. Org. Chem., 56:5623-5630 (1991).

Bartzatt et al., "Synthesis and Analysis of a Methyl Ether Derivative of Tetracycline Which Inhibits Growth of *Escherichia Coli*", Physiol. Chem. Phys. & Med. NMR, 34:71-81 (2002).

Bartzatt et al., "Synthesis and Analysis of Ethylated Tetracycline, an Antibiotic Derivative that Inhibits the Growth of Tetracycline-Resistant XL I-Blue Bacteria", Biotechnol. Appl. Biochem., 33:65-69 (2001).

(Continued)

*Primary Examiner* — Jeffrey S Lundgren
*Assistant Examiner* — Sara E Townsley
(74) *Attorney, Agent, or Firm* — McCarter & English, LLP; Elizabeth A. Hanley

(57) ABSTRACT

Methods and compositions for the treatment of skin disorders (e.g., acne, rosacea) are described.

10 Claims, 1 Drawing Sheet

(56) References Cited

U.S. PATENT DOCUMENTS

| | | |
|---|---|---|
| 5,998,390 A | 12/1999 | Ramamurthy et al. |
| 6,015,804 A | 1/2000 | Golub et al. |
| 6,043,225 A | 3/2000 | Shor et al. |
| 6,043,231 A | 3/2000 | Pruzanski et al. |
| 6,100,248 A | 8/2000 | Golub et al. |
| 6,231,894 B1 | 5/2001 | Stamler et al. |
| 6,256,365 B1 | 7/2001 | Lai |
| 6,277,061 B1 | 8/2001 | Golub et al. |
| 6,500,812 B2 | 12/2002 | Nelson et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,202,235 B2 | 4/2007 | Levy et al. |
| 7,208,482 B2 | 4/2007 | Garcia-Luzon et al. |
| 7,323,492 B2 | 1/2008 | Huss et al. |
| 7,326,696 B2 | 2/2008 | Nelson et al. |
| 7,361,674 B2 | 4/2008 | Nelson et al. |
| 7,414,041 B2 | 8/2008 | Levy |
| 7,521,437 B2 | 4/2009 | Nelson et al. |
| 7,553,828 B2 | 6/2009 | Nelson et al. |
| 8,318,706 B2 | 11/2012 | Kim et al. |
| 2003/0069721 A1 | 4/2003 | Podlogar |
| 2004/0138183 A1 | 7/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2005/0020545 A1 | 1/2005 | Draper et al. |
| 2005/0038002 A1 | 2/2005 | Nelson et al. |
| 2005/0070510 A1 | 3/2005 | Draper et al. |
| 2005/0143352 A1 | 6/2005 | Nelson et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0166944 A1 | 7/2006 | Berniac et al. |
| 2006/0166945 A1 | 7/2006 | Abato et al. |
| 2006/0166946 A1 | 7/2006 | Nelson et al. |
| 2006/0194773 A1 | 8/2006 | Levy et al. |
| 2006/0281717 A1 | 12/2006 | Berniac et al. |
| 2006/0287283 A1 | 12/2006 | Amoo et al. |
| 2007/0072834 A1 | 3/2007 | Nelson et al. |
| 2007/0093455 A1 | 4/2007 | Abato et al. |
| 2007/0167415 A1 | 7/2007 | Levy et al. |
| 2007/0270389 A1 | 11/2007 | Garcia-Luzon et al. |
| 2008/0015169 A1 | 1/2008 | Nelson et al. |
| 2008/0070873 A1 | 3/2008 | Alekshun et al. |
| 2008/0118979 A1 | 5/2008 | Draper et al. |
| 2008/0167273 A1 | 7/2008 | Nelson et al. |
| 2008/0287401 A1 | 11/2008 | Johnston et al. |
| 2008/0300424 A1 | 12/2008 | Nelson et al. |
| 2008/0306032 A1 | 12/2008 | Nelson et al. |
| 2009/0054379 A1 | 2/2009 | Huss et al. |
| 2009/0118269 A1 | 5/2009 | Berniac et al. |
| 2009/0124528 A1 | 5/2009 | Nelson et al. |
| 2009/0131696 A1 | 5/2009 | Levy |
| 2009/0156842 A1 | 6/2009 | Seyedi et al. |

FOREIGN PATENT DOCUMENTS

| | | |
|---|---|---|
| GB | 921252 A | 3/1963 |
| GB | 1108310 A | 4/1968 |
| GB | 1469384 A | 4/1977 |
| WO | 9522529 A1 | 8/1995 |
| WO | 9634852 A1 | 11/1996 |
| WO | 0119784 A1 | 3/2001 |
| WO | 0204406 A2 | 1/2002 |
| WO | 0204407 A2 | 1/2002 |
| WO | 02072022 A2 | 9/2002 |
| WO | 02072506 A2 | 9/2002 |
| WO | 02072532 A1 | 9/2002 |
| WO | 03005971 A2 | 1/2003 |
| WO | 03057169 A2 | 7/2003 |
| WO | 03075857 A2 | 9/2003 |
| WO | 03079984 A2 | 10/2003 |
| WO | 03088906 A2 | 10/2003 |
| WO | 2004064728 A2 | 8/2004 |
| WO | 2004091513 A2 | 10/2004 |
| WO | 2005009943 A2 | 2/2005 |
| WO | 2005082860 A1 | 9/2005 |
| WO | 2006047756 A2 | 5/2006 |
| WO | 2007014154 A2 | 2/2007 |
| WO | 2007133797 A2 | 11/2007 |
| WO | 2007133798 A2 | 11/2007 |
| WO | 2008045507 A2 | 4/2008 |
| WO | 2008079339 A2 | 7/2008 |

OTHER PUBLICATIONS

Berens et al., "Subtype Selective Tetracycline Agonists and their Application for a Two-Stage Regulatory System", Chem. Bio. Chem., 7:1320-1324 (2006).

Boothe et al., "6-Deoxtetracyclines. I. Chemical Modifications by Electrophilic Substitution", Am. Chem. Soc., 82(5):1253-1254 (1960).

Chandler et al., J. Neuroimmunol., 72:155-61 (1997).

Greenwald et al., Bone, 22:33-38 (1998).

Koza et al., "Palladium Catalyzed C—N Bond Formation in the Synthesis of 7-Amino-Substituted Tetracyclines", J. Org. Chem., 67:5025-5027 (2002).

Koza et al., "Synthesis and Biological Evaluation of 9-Substituted Tetracycline Derivatives", Bioorg. Med. Chem. Lett., 12(16):2163-2165 (2002).

Koza, D.J., "Synthesis of 7-Substituted Tetracycline Derivatives", Org. Lett., 2(6):815-817 (2000).

Koza, D.J., "The Synthesis of 8-Substituted Tetracycline Derivatives, the First 8-Position Carbon-Carbon Bond", Tetrahedron Lett., 41:5017-5020 (2000).

Lew et al., "Antifungal Activity of Four Tetracycline Analogues against Candida albicans in Vitro: Potentiation by Amphotericin B", J. Infect. Dis., 136(2):263-270 (1977).

Li et al., Mol. Carcinog. 22:84-89 (1998).

Liedtke et al., Ann. Neurol. 44:35-46 (1998).

Martell et al., "The 6-Deoxytetracyclines. IX. Imidomethylation", J. Med Chem.,10(3):359-363 (1967).

Nelson et al., "Inhibition of theTetracycline Efflux Antiport Protein by 13-Thio-Substituted 5-Hydroxy-6-Deoxytetracyclines", J. Med. Chem., 36(3):370-377 (1993).

Paemen et al., "The Gelatinase Inhibitory Activity of Tetracyclines and Chemically Modified Tetracycline Analogues as Measured by a Novel Microtiter Assay for Inhibitors", Biochem. Pharm., 52:105-111 (1996).

Petersen et al., "In Vitro and In Vivo Antibacterial Activities of a Novel Glyclycycline, the 9-t-Butylglycylamido Derivative of Minocycline (GAR-936)", Antimicrobial Agents Chemo., 43(4):738-744 (1999).

Ryan et al., Curr. Op. Rheumatol., 8:238-247 (1996).

Spencer et al., "6-Deoxytetracyclines. V. 7,9-Disubstituted Products", J. Med. Chem., 122:405-407 (1963).

Stetler-Stevenson et al., Annu. Rev. Cell Biol., 9:541-73 (1993).

Sum et al., "Glycylcyclines. 1. A New Generation of Potent Antibacterial Agents through Modification of 9-Aminotetracyclines", J. Med. Chem., 37(1):184-188 (1994).

Sum et al., "Recent Developments in Tetracycline Antibiotics", Curr. Pharm. Des., 4(2):119-132 (1998).

(56) References Cited

OTHER PUBLICATIONS

Sum et al., "Synthesis and Antibacterial Activity of 9-Substituted Minocycline Derivatives", Bioorg. Med. Chem. Lett., 16:400-403 (2006).
Tally et al., "Glycylcyclines: a New Generation of Tetracyclines", J. Antimicrobial Chem., 35:449-452 (1995).
Tryggvason et al., Biochim. Biophys. Acta, 907:191-217 (1987).
Van den Bogert et al., "Doxycycline in Combination Chemotherapy of a Rat Leukemia", Cancer Research, 48, 6686-6690 (1988).
Waitz, J.A., CLSI, Document M7-A2, 10:8, 13-20, 2nd ed., Villanova, PA (1990).

SUBSTITUTED TETRACYCLINE COMPOUNDS FOR TREATMENT OF INFLAMMATORY SKIN DISORDERS

RELATED APPLICATIONS

This application is a continuation of U.S. patent application Ser. No. 11/963,509, filed Dec. 21, 2007 (now U.S. Pat. No. 8,513,223, issuing Aug. 20, 2013), which claims the benefit of U.S. provisional patent application Ser. No. 60/876,434, filed Dec. 21, 2006. The entire contents of each of these applications are hereby incorporated herein by reference.

BACKGROUND OF THE INVENTION

Acne is a disorder resulting from the actions of hormones on the sebaceous glands, which leads to plugged pores and outbreaks of lesions, commonly called pimples. Nearly 17 million people in the United States have acne, making it the most common skin disease. Severe acne can lead to disfiguring, permanent scarring.

Acne is described as a disorder of the pilosebaceous units (PSUs). Found over most of the body, PSUs consist of a sebaceous gland connected to a canal, called a follicle that contains a fine hair. These units are most numerous on the face, upper back and chest. The sebaceous glands make an oily substance called sebum that normally empties onto the skin surface through the opening of the follicle, also called a pore. Cells called keratinocytes line the follicle.

The hair, sebum and keratinocytes that fill the narrow follicle may produce a plug, which is an early sign of acne. The plug prevents sebum from reaching the surface of the skin through a pore. The mixture of oil and cells allows bacteria *Propionibacterium acnes.* (*P. acnes*) that normally live on the skin to grow in the plugged follicles. The bacteria produce chemicals and enzymes and attract white blood cells that cause inflammation. Then the wall of the plugged follicle breaks down, the sebum, shed skin cells and bacteria disseminate into the nearby tissues, leading to lesions or pimples.

For patients with moderate to severe acne, the doctor often prescribes oral antibiotics. Oral antibiotics are thought to help control acne by curbing the growth of bacteria and reducing inflammation. Tetracyclines have been used because of their anti-bacterial and anti-inflammatory properties.

SUMMARY OF THE INVENTION

In one embodiment, the present invention pertains, at least in part, to a method for treating an inflammatory skin disorder in a subject by administering an effective amount of a substituted tetracycline compound to the subject. Advantageously, the substituted tetracycline compounds used in the methods of the invention have one or more of the following characteristics: 1) narrow spectrum anti-bacterial activity against gram-positive bacteria; 2) anti-inflammatory activity; 3) less phototoxicity than doxycycline; and 4) oxidatively more stability than minocycline.

In another embodiment, the present invention pertains, at least in part, to a method of treating an inflammatory skin disorder in a subject by administering an effective amount of a substituted tetracycline compound of formula I:

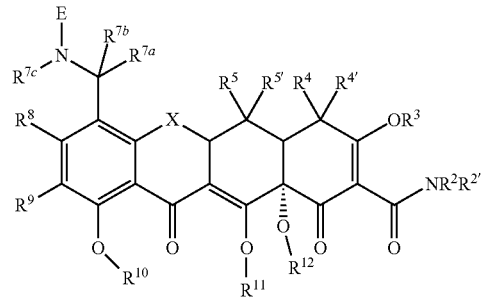

wherein
X is $CHC(R^{13}Y'Y)$, $CR^{6}R^{6}$, $C=CR^{6'}R^{6}$, S, $NR^{6}$, or O;
E is $NR^{7d}R^{7e}$, $OR^{7f}$, or $(CH_2)_{0-1}C(=W')WR^{7g}$;
W is O, S, $NR^{7h}$, or $CR^{7i}R^{7j}$;
W' is O, S, or $NR^{7k}$;
$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^3$, $R^{10}$, $R^{11}$ and $R^{12}$ are each hydrogen or a prodrug moiety;
$R^4$ is $NR^{4a}R^{4b}$, alkyl, alkenyl, alkynyl, hydroxyl, halogen, or hydrogen;
$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^{7a}$, $R^{7b}$, $R^{7c}$, $R^{7d}$, $R^{7e}$, $R^{7f}$, $R^{7g}$, $R^{7h}$, $R^{7i}$, $R^{7k}$ and $R^{7j}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, or arylcarbonyloxy, or $R^{7c}$ and $R^{7d}$ or $R^{7c}$ and $R^{7f}$ are linked to form a ring;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, or $-(CH_2)_{0-3}(NR^{9c})_{0-1}C(=Z')ZR^{9a}$;
Z is $CR^{9d}R^{9e}$, S, $NR^{9b}$ or O;
Z' is O, S, or $NR^{9f}$;
$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains, at least in part, to a method of treating an inflammatory skin disorder in a subject by administering an effective amount of a substituted tetracycline compound of formula II:

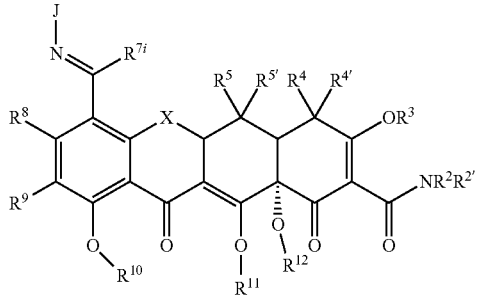

(II)

wherein
X is CHC(R$^{13}$Y'Y), CR$^{6'}$R$^6$, C≡CR$^{6'}$R$^6$, S, NR$^6$, or O;
J is NR$^{7m}$R$^{7n}$, OR$^{7o}$ or heteroaryl;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{10}$, R$^{11}$ and R$^{12}$ are each hydrogen or a prodrug moiety;
R$^4$ is NR$^{4a}$R$^{4b}$, alkyl, alkenyl, alkynyl, hydroxyl, halogen, or hydrogen;
R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7i}$, R$^{7m}$, R$^{7n}$ and R$^{7o}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;
Z is CR$^{9d}$R$^{9e}$, S, NR$^{9b}$ or O;
Z' is O, S, or NR$^{9f}$;
R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In yet another embodiment, the invention pertains, at least in part, to a method for treating an inflammatory skin disorder in a subject by administering to the subject an effective amount of a substituted tetracycline compound of formula III:

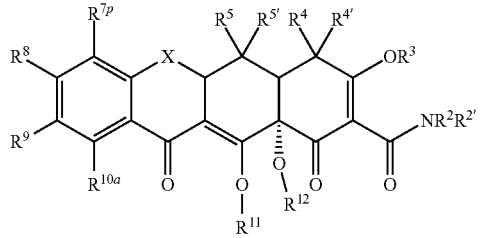

(III)

wherein
X is CHC(R$^{13}$Y'Y), CR$^{6'}$R$^6$, C≡CR$^{6'}$R$^6$, S, NR$^6$, or O;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{11}$ and R$^{12}$ are each hydrogen or a prodrug moiety;
R$^4$ is NR$^{4a}$R$^{4b}$, alkyl, alkenyl, alkynyl, hydroxyl, halogen, or hydrogen;
R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7p}$ is hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;
Z is CR$^{9d}$R$^{9e}$, S, NR$^{9b}$ or O;
Z' is O, S, or NR$^{9f}$;
R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{10a}$ is hydrogen;
R$^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, the present invention pertains, at least in part, to a method for treating an inflammatory skin disorder in a subject by administering to the subject an effective amount of a substituted tetracycline compound of formula IV:

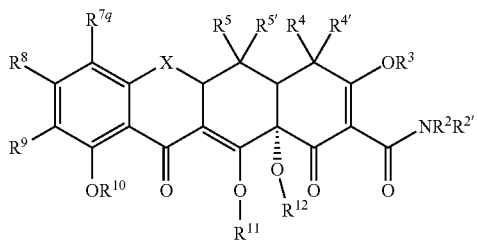

(IV)

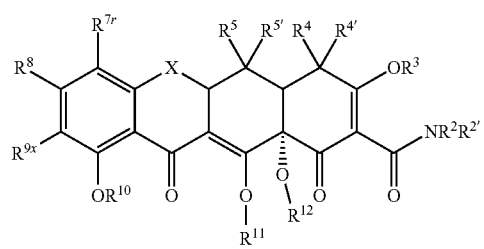

(V)

wherein

X is CHC($R^{13}$Y'Y), $CR^{6'}R^6$, C=$CR^{6'}R^6$, S, $NR^6$, or O;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7q}$ is heteroaryl;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In yet another embodiment, the present invention pertains, at least in part, to a method of treating an inflammatory skin disorder in a subject by administering to the subject an effective amount of a substituted tetracycline compound of formula V:

wherein

X is CHC($R^{13}$Y'Y), $CR^{6'}R^6$, C=$CR^{6'}R^6$, S, $NR^6$, or O;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7r}$ is hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{9x}$ is CN, $CR^{9g}NR^{9h}$ or $CR^{9i}R^{9j}NR^{9k}R^{9l}$;

$R^{9g}$, $R^{9h}$, $R^{9i}$, $R^{9j}$, $R^{9k}$ and $R^{9l}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the present invention pertains, at least in part, to a method for treating an inflammatory skin disorder in a subject by administering an effective amount of a substituted tetracycline compound of formula VI:

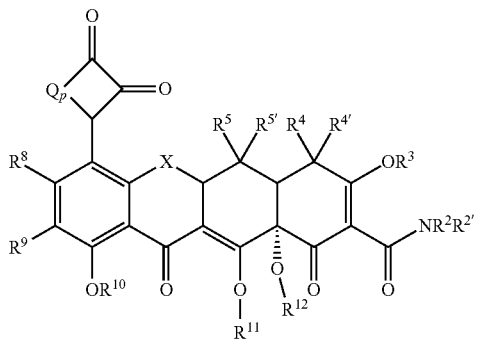

(VI)

wherein
X is CHC(R$^{13}$Y'Y), CR$^{6'}$R$^6$, C≡CR$^{6'}$R$^6$, S, NR$^6$, or O;
p is a single bond or a double bond;
Q is CR$^{7s}$ when p is a double bond or Q is CR$^{7s'}$R$^{7s''}$ when p is a single bond;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{10}$, R$^{11}$ and R$^{12}$ are each hydrogen or a pro-drug moiety;
R$^4$ is NR$^{4a}$R$^{4b}$, alkyl, alkenyl, alkynyl, hydroxyl, halogen, or hydrogen;
R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7s}$, R$^{7s'}$ and R$^{7s''}$ are each hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;
Z is CR$^{9d}$R$^{9e}$, S, NR$^{9b}$ or O;
Z' is O, S, or NR$^{9f}$;
R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains, at least in part, to a pharmaceutical composition comprising a pharmaceutically acceptable carrier and an effective amount of a substituted tetracycline compound for the treatment of an inflammatory skin disorder, wherein said compound is of formula I, II, III, IV, V or VI.

DETAILED DESCRIPTION OF THE INVENTION

Figure 1:
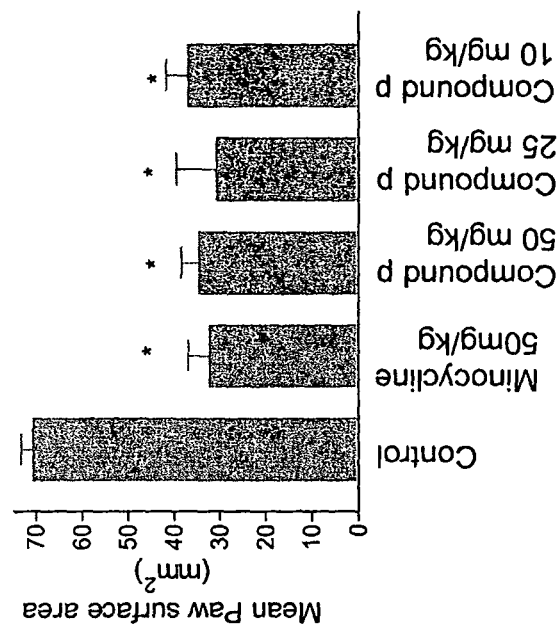
FIG. 1 is a graphical comparison of the modulation of carregeenan induced inflammation in the rat paw edema model between doxycycline and compound A.

In one embodiment, the present invention is directed to a method for treating an inflammatory skin disorder in a subject by administering an effective amount of a substituted tetracycline compound to the subject. Advantageously, the tetracycline compound used in the methods of the invention has one or more of the following characteristics: 1) narrow spectrum anti-bacterial activity against gram-positive bacteria; 2) anti-inflammatory activity; 3) a phototoxicity less than or equal to doxycycline; and 4) an oxidative potential less than or equal to minocycline.

The term "inflammatory skin disorder" includes, for example, eczema, dermatitis, psoriasis, pyoderma gangrenosum, acne and rosacea.

The term "subject" includes animals (e.g., mammals, e.g., cats, dogs, horses, pigs, cows, sheep, rodents, rabbits, squirrels, bears, primates (e.g., chimpanzees, gorillas, and humans)) which are capable of (or currently) suffering from an inflammatory skin disorder. It also includes transgenic animal models.

The term "treated," "treating" or "treatment" includes therapeutic and/or prophylactic treatment of inflammatory skin disorders. The treatment includes the diminishment or alleviation of at least one symptom associated with an inflammatory skin disorder. For example, treatment can be diminishment of one or several symptoms of the inflammatory skin disorder or complete eradication of the inflammatory skin disorder.

The language "effective amount" of the tetracycline compound is that amount necessary or sufficient to treat or prevent the inflammatory skin disorder in a subject, e.g. prevent the various symptoms of the inflammatory skin disorder. The effective amount can vary depending on such factors as the size and weight of the subject, the type of inflammatory skin disorder, or the particular tetracycline compound. For example, the choice of the tetracycline compound can affect what constitutes an "effective amount." One of ordinary skill in the art would be able to study the aforementioned factors and make the determination regarding the effective amount of the tetracycline compound without undue experimentation.

The term "tetracycline compound" includes substituted tetracycline compounds or compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

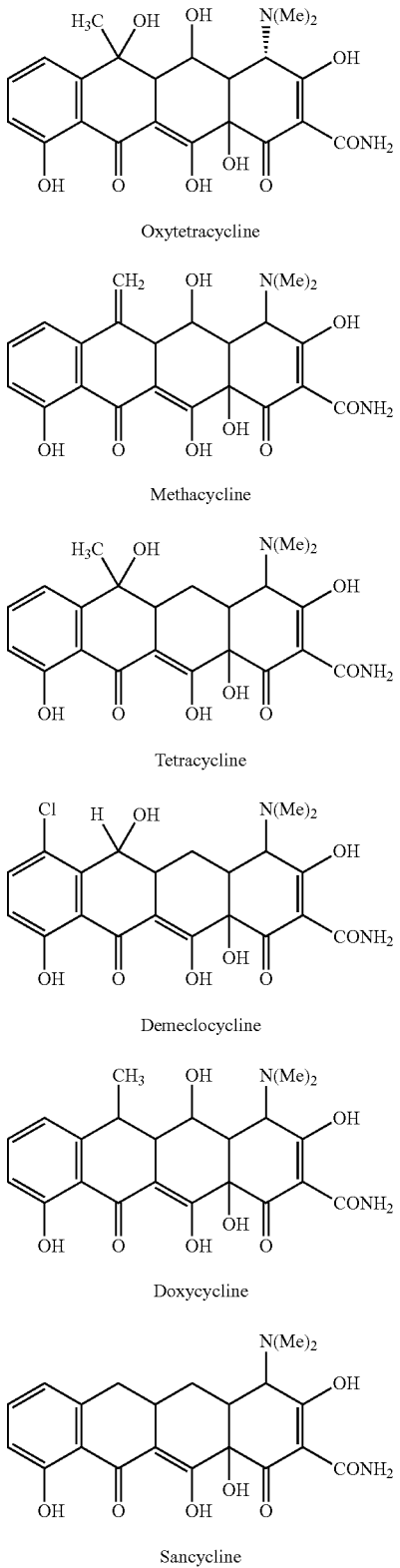

Oxytetracycline

Methacycline

Tetracycline

Demeclocycline

Doxycycline

Sancycline

TABLE 1-continued

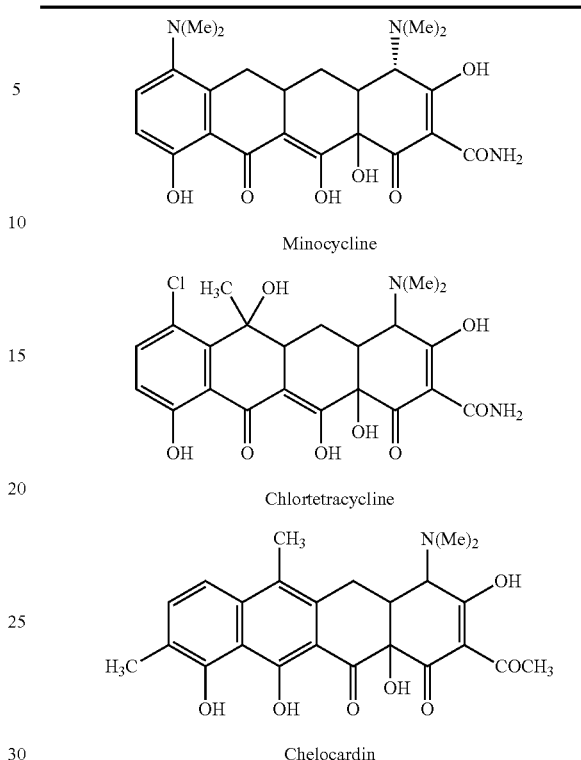

Minocycline

Chlortetracycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a C1-6, 12 hemiketal tetracyclines; 11a C1-6-methylene tetracyclines; 6, 13 diol tetracyclines; 6-benzylthiomethylene tetracyclines; 7,11a-dichloro-6-fluoro-methyl-6-deoxy tetracyclines; 6-fluoro(α)-6-demethyl-6-deoxy tetracyclines; 6-fluoro (β)-6-demethyl-6-deoxy tetracyclines; 6-α acetoxy-6-demethyl tetracyclines; 6-13 acetoxy-6-demethyl tetracyclines; 7,13-epithiotetracyclines; oxytetracyclines; pyrazolotetracyclines; 11a halogens of tetracyclines; 12a formyl and other esters of tetracyclines; 5, 12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The term "substituted tetracycline compound" includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function, e.g., treat a skin disorder. Preferably, the substituted tetracycline compounds of the invention are compounds of formual I, II, III, W, V or VI. It does not include unsubstituted minocycline, unsubstituted doxycycline or sancycline.

In one embodiment, the substituted tetracycline compound has an MIC (e.g., as measured in Example 2) of between about 0.001 to 64 μg/mL, preferably between about 0.001 and 16 μg/mL and more preferably between about 0.001 and 4 μg/mL.

In one embodiment, the substituted tetracycline compound exhibits antibacterial activity. In another embodiment, the substituted tetracycline compound exhibits anti-inflammatory activity. In yet another embodiment, the substituted tetracycline compound exhibits both antibacterial and anti-inflammatory activities. The term "anti-inflammatory activity" includes activity that prevents, reduces or ameliorates the symptoms of acute or chronic inflammation. The substituted tetracycline compounds of the invention may treat, prevent, reduce or ameliorate the symptoms of inflammation (e.g., redness, swelling, heat, pain, loss of function, tissue destruction, etc.) and/or may effect the biochemical pathways that cause inflammation in the body to treat, prevent, reduce or ameliorate inflammation.

In a further embodiment, the substituted tetracycline compounds of the invention may have one or more; two or more; three or more; or all of the following characteristics: 1) narrow spectrum anti-bacterial activity; 2) anti-inflammatory activity; 3) a phototoxicity less than or equal to doxycycline and 4) an oxidative potential less than or equal to minocycline.

In a further embodiment, the substituted tetracycline compound may have narrow spectrum antibiotic activity. The term "narrow spectrum" includes activity against specific types of bacteria. In one embodiment, the substituted tetracycline compounds exhibit greater antibacterial activity against gram positive bacteria than against gram negative bacteria. Examples of gram positive bacteria include, for example, S. aureus, S. pneumoniae, P. granulosum and P. acnes.

In one embodiment, the substituted tetracycline compound used in the methods of the invention has an MIC of less than about 64 μg/mL, less than about 32 μg/mL, less than about 16 μg/mL, less than about 8 μg/mL, less than about 4 μg/mL or less than about 1 μg/mL against gram positive bacteria, e.g., P. acnes, and/or P. granulosum.

In one embodiment, the substituted tetracycline compound used in the methods of the invention has a minimum inhibitory concentration (MIC) less than that of doxycycline or minocycline for S. aureus, P. granulosum, S. pneumoniae, or P. acnes.

In another embodiment, the tetracycline compounds of the invention have narrow spectrum antibacterial activity. The term "narrow spectrum" includes tetracycline compounds which do have substantial antibacterial activity against gram positive bacteria, e.g., tetracycline compounds with an MIC of less than about 64 μg/mL, less than about 32 μg/mL, less than about 16 μg/mL, less than about 8 μg/mL, less than about 4 μg/mL or less than about 1 μg/mL against S. aureus, P. granulosum, P. acnes or S. pneumoniae (e.g., as tested in the assay described in Example 2).

The term "narrow spectrum" includes tetracycline compounds which do not have substantial antibacterial activity against gram negative bacteria, e.g., tetracycline compounds with an MIC of greater than about 1 μg/mL, greater than about 4 μg/mL, greater than about 8 μg/mL, greater than about 16 μg/mL, greater than about 32 μg/mL, or greater than about 64 μg/mL against gram negative bacteria such as E. coli or B. thetaiotaomicron (e.g., as tested in the assay described in Example 2).

In another embodiment, the substituted tetracycline compounds used in the methods of the invention has anti-inflamatory activity, e.g., as determined in the rat-paw edema model described in Example 7.

In another embodiment, the substituted tetracycline compounds used in the methods of the invention have a phototoxicity equal to or less than that of doxycycline (e.g., such as measured in the assay described in Example 4). In yet another embodiment, the substituted tetracycline compounds used in the methods of the invention have an oxidative potential less than or equal to the oxidative potential of minocycline (e.g., such as measured in the assay described in Example 5).

In one embodiment, the substituted tetracycline compound of the invention is of the formula I:

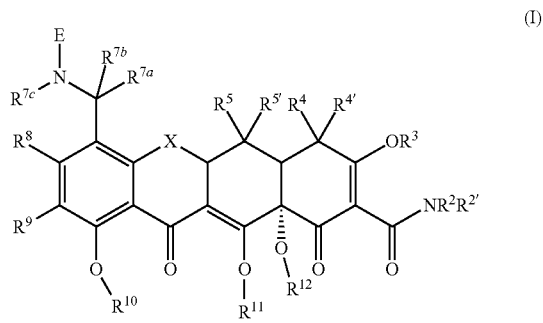

(I)

wherein

X is CHC($R^{13}$Y'Y), $CR^{6'}R^6$, C=$CR^{6'}R^6$, S, $NR^6$, or O;

E is $NR^{7d}R^{7e}$, $OR^{7f}$, or $(CH_2)_{0-1}C(=W')WR^{7g}$;

W is O, S, $NR^{7h}$, or $CR^{7i}R^{7j}$;

W' is O, S, or $NR^{7k}$;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a prodrug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7a}$, $R^{7b}$, $R^{7c}$, $R^{7d}$, $R^{7e}$, $R^{7f}$, $R^{7g}$, $R^{7h}$, $R^{7i}$, $R^{7k}$ and $R^{7j}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, or arylcarbonyloxy, or $R^{7c}$ and $R^{7d}$ or $R^{7e}$ and $R^{7f}$ are linked to form a ring;

R[8] is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R[9] is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, or —(CH$_2$)$_{0-3}$(NR$^{9c}$)$_{0-1}$C(=Z')ZR$^{9a}$;

Z is CR$^{9d}$R$^{9e}$, S, NR$^{9b}$ or O;

Z' is O, S, or NR$^{9f}$;

R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is CR$^{6'}$R$^6$, R$^4$ is NR$^{4a}$R$^{4b}$, R$^{4a}$ and R$^{4b}$ are each alkyl (e.g., methyl); R$^2$, R$^{2'}$, R$^3$, R$^4$, R$^5$, R$^{5'}$ R$^6$, R$^{6'}$, R$^{7a}$, R$^{7b}$, R$^{7c}$, R$^8$, R$^9$, R$^{10}$, R$^{11}$ and R$^{12}$ are each hydrogen; E is OR$^{7f}$; R$^{7f}$ is allyl (e.g., CH$_2$=CHCH$_2$—) or alkyl (e.g., ethyl; isopropyl; t-butyl; alkoxy substituted alkyl (e.g., methoxyethyl); halogen substituted alkyl (e.g., alkyl substituted with fluorine, for example, FCH$_2$CH$_2$—; F$_2$CHCH$_2$—; CF$_3$CH$_2$— or CF$_2$H—); alkylcarbonylalkyl (e.g., CH$_3$CO(CH$_2$)$_n$—, in which n is an integer from 0-6, for example 1); alkoxycarbonylalkyl (e.g., CH$_3$OCO (CH$_2$)$_m$—, in which m is an integer from 0-6, for example 1) or carboxylatealkyl (HOOC(CH$_2$)$_q$—, in which q is an integer from 0-6, for example 1).

In one embodiment, X is CR$^{6'}$R$^6$, R$^4$ is NR$^{4a}$R$^{4b}$, R$^{4a}$ and R$^{4b}$ are each alkyl (e.g., methyl); R$^2$, R$^{2'}$, R$^3$, R$^4$ R$^5$, R$^{5'}$ R$^6$, R$^{6'}$, R$^{7a}$, R$^{7b}$, R$^8$, R$^9$, R$^{10}$, R$^{11}$ and R$^{12}$ are each hydrogen; E is OR$^{7f}$ and R$^{7c}$ and R$^{7f}$ are linked to join a ring, for example, a 5- or 6-membered ring (e.g.,

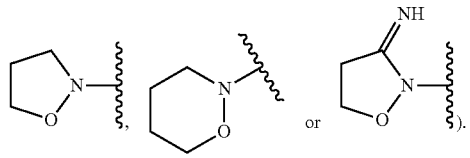

).

In another embodiment, X is CR$^{6'}$R$^6$, R$^4$ is NR$^{4a}$R$^{4b}$, R$^{4a}$ and R$^{4b}$ are each alkyl (e.g., methyl); R$^2$, R$^{2'}$, R$^3$, R$^4$ R$^5$, R$^{5'}$ R$^6$, R$^{6'}$, R$^{7a}$, R$^{7b}$R$^8$, R$^9$, R$^{10}$, R$^{11}$ and R$^{12}$ are each hydrogen; E is OR$^{7f}$; R$^{7c}$ and R$^{7f}$ may be each independently alkyl (e.g., methyl or ethyl).

In yet another embodiment, X is CR$^{6'}$R$^6$, R$^4$ is NR$^{4a}$R$^{4b}$, R$^{4a}$ and R$^{4b}$ are each alkyl (e.g., methyl); R$^2$, R$^{2'}$, R$^3$, R$^4$ R$^5$, R$^{5'}$ R$^6$, R$^{6'}$, R$^{7a}$, R$^{7b}$, R$^{7c}$, R$^8$, R$^9$, R$^{10}$, R$^{11}$ and R$^{12}$ are each hydrogen; E is NR$^{7d}$R$^{7e}$; R$^{7c}$ is alkyl (e.g., ethyl); R$^{7d}$ is hydrogen and R$^{7e}$ is alkyl (e.g., ethyl).

In another embodiment, X is CR$^{6'}$R$^6$, R$^4$ is NR$^{4a}$R$^{4b}$, R$^{4a}$ and a are each alkyl (e.g., methyl); R$^2$, R$^{2'}$, R$^3$, R$^4$ R$^5$, R$^{5'}$ R$^6$, R$^{6'}$, R$^{7a}$, R$^{7b}$, R$^{7c}$, R$^8$, R$^9$, R$^{10}$, R$^{11}$ and R$^{12}$ are each hydrogen; E is —C(=W')WR$^{7g}$; W and W' are each oxygen; R$^{7c}$ is allyl (e.g., CH$_2$=CHCH$_2$—) and R$^{7g}$ is alkoxy (e.g., methoxy).

In one embodiment, X is CR$^{6'}$R$^6$, R$^4$ is NR$^{4a}$R$^{4b}$, R$^{4a}$ and a are each alkyl (e.g., methyl); R$^2$, R$^{2'}$, R$^3$, R$^4$ R$^5$, R$^{5'}$ R$^6$, R$^{6'}$, R$^{7a}$, R$^{7b}$, R$^{7c}$, R$^8$, R$^9$, R$^{10}$, R$^{11}$ and R$^{12}$ are each hydrogen; E is —CH$_2$(C=W')WR$^{7g}$; R$^{7c}$ is alkyl (e.g., methyl); W is CR$^{7i}$R$^{7j}$; R$^{7j}$ and leg are each hydrogen; W' is NR$^{7k}$ and R$^{7k}$ is alkoxy (e.g., ethoxy).

Examples of substituted tetracycline compounds of formula I include, for example:

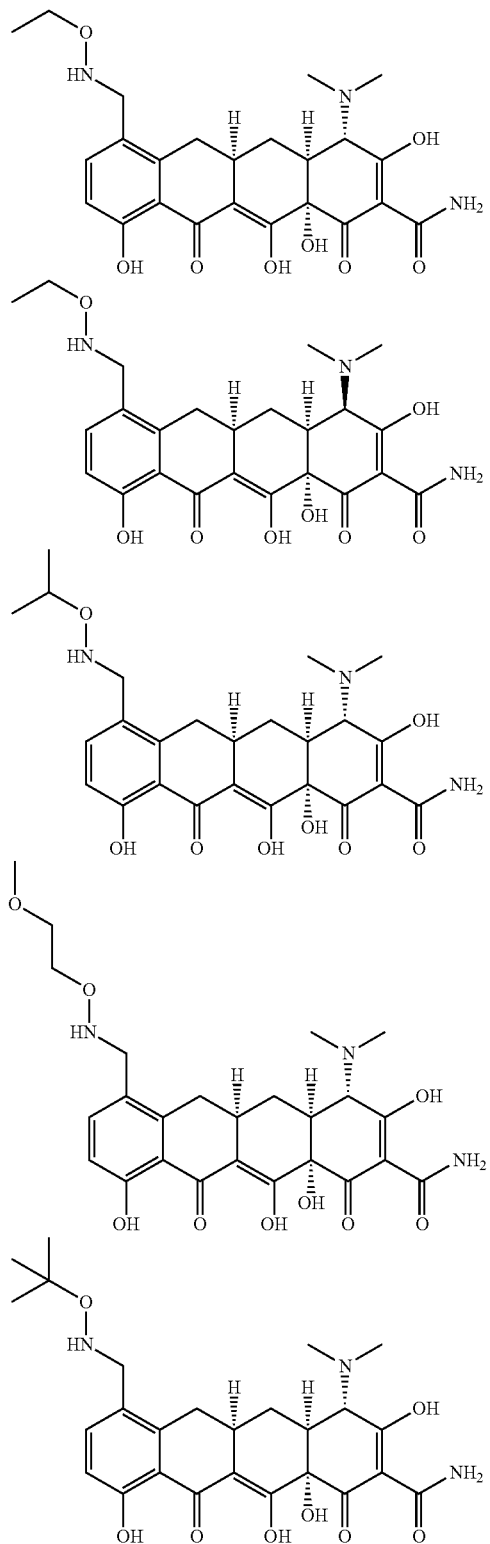

15
-continued
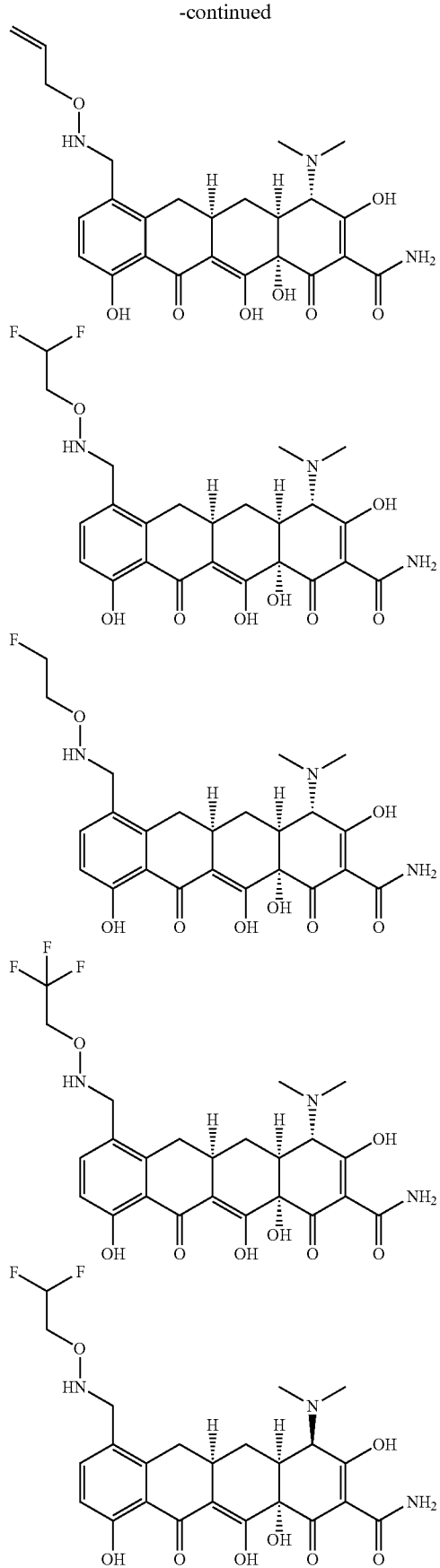
16
-continued
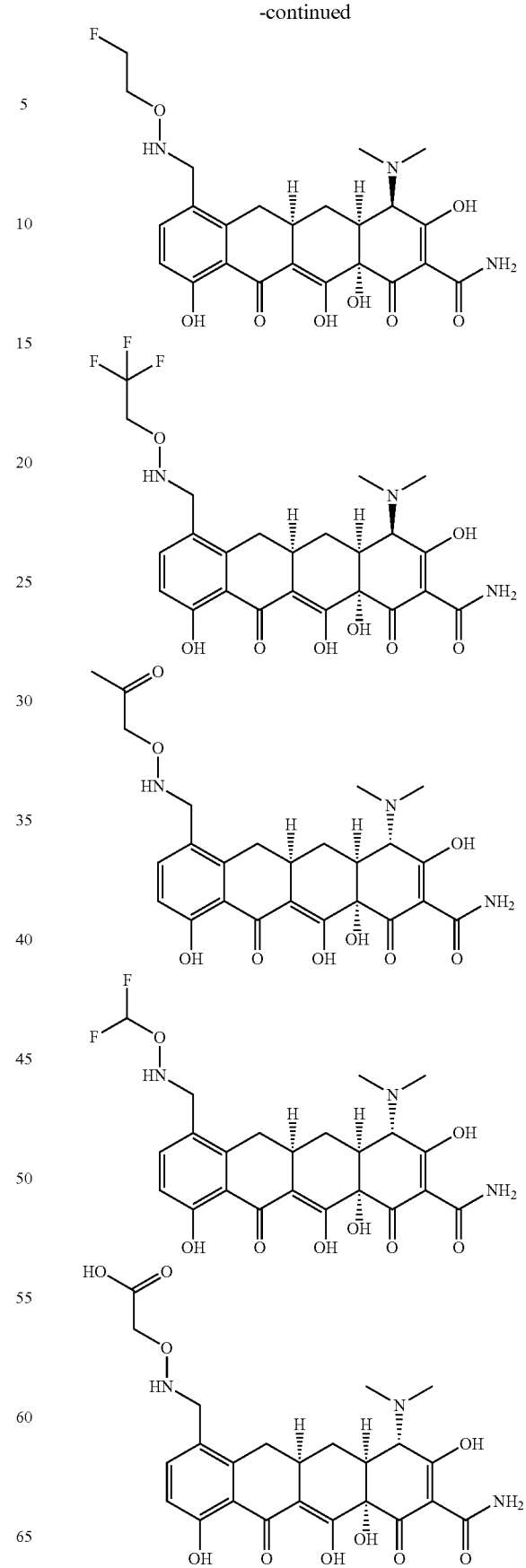

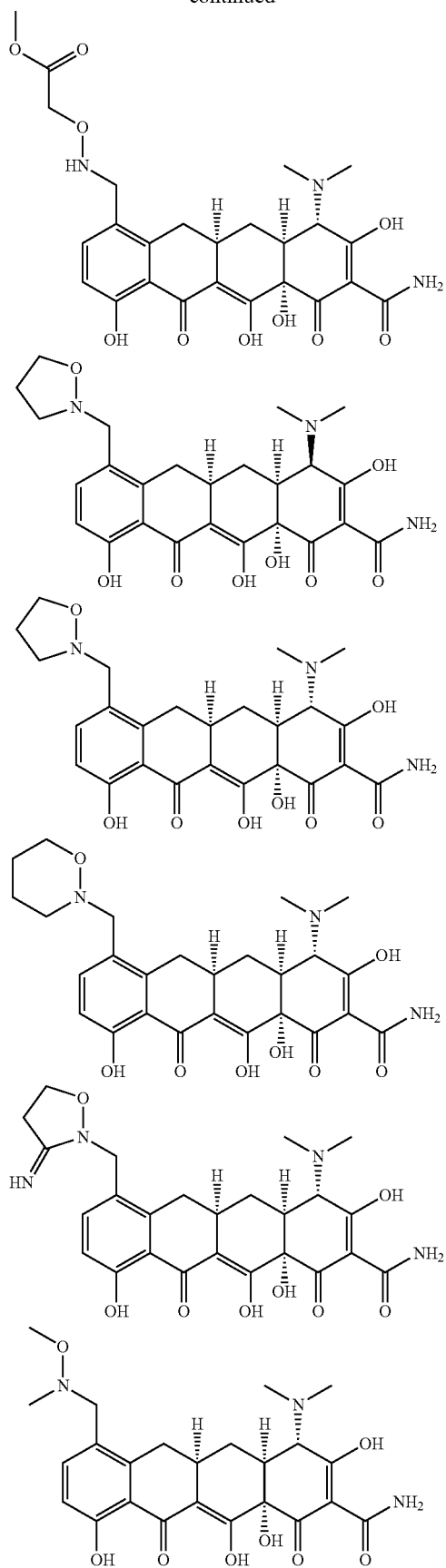
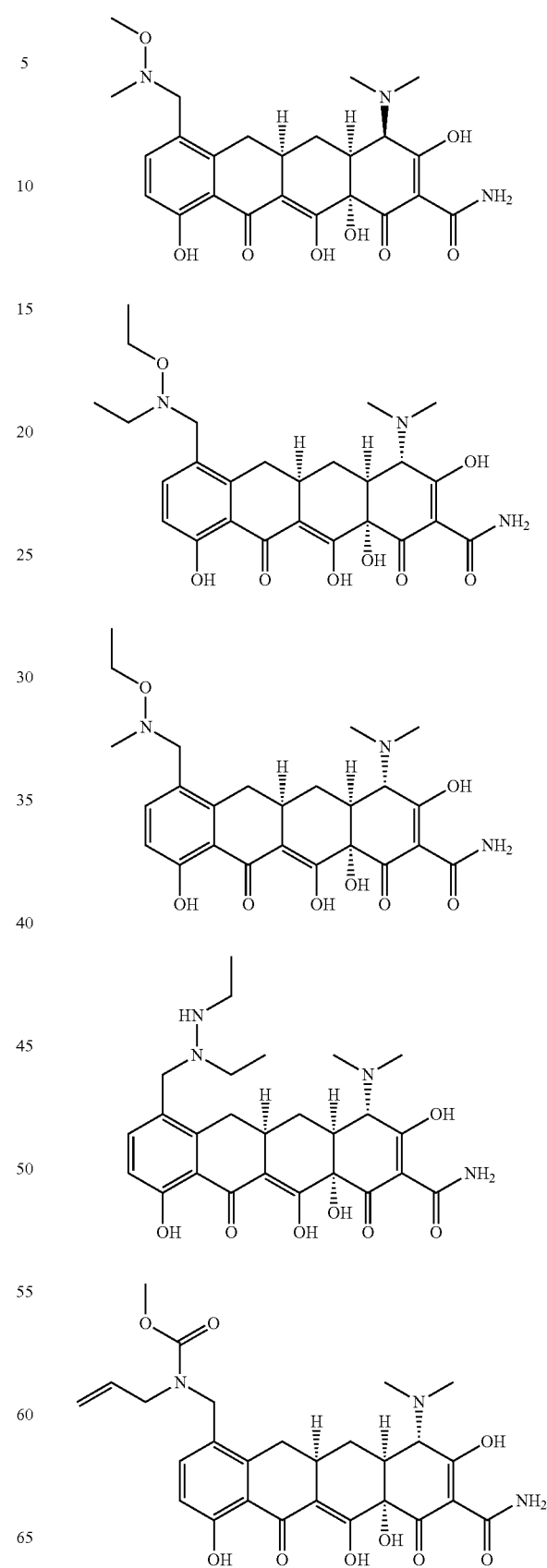

-continued

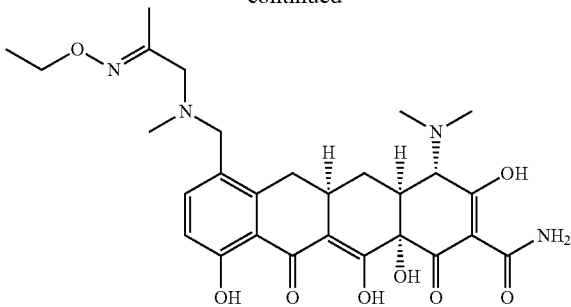

and pharmaceutically acceptable salts thereof.

In another embodiment, the substituted tetracycline compound of the invention is a compound of formula II:

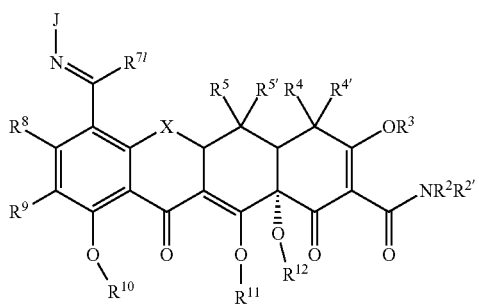

wherein

X is $CHC(R^{13}Y'Y)$, $CR^{6'}R^6$, $C=CR^{6'}R^6$, S, $NR^6$, or O;
J is $NR^{7m}R^{7n}$, $OR^{7o}$ or heteroaryl;
$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, aryl alkyl, aryl, heterocyclic, heteroaromatic or a prodrug moiety;
$R^3$, $R^{10}$, $R^{11}$ and $R^{12}$ are each hydrogen or a prodrug moiety;
$R^4$ is $NR^{4a}R^{4b}$, alkyl, alkenyl, alkynyl, hydroxyl, halogen, or hydrogen;
$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^{7l}$, $R^{7m}$, $R^{7n}$ and $R^{7o}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or $-(CH_2)_{0-3}(NR^{9c})_{0-1}C(=Z')ZR^{9a}$;
Z is $CR^{9d}R^{9e}$, S, $NR^{9b}$ or O;
Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6'}R^6$, $R^4$ is $NR^{4a}R^{4b}$, $R^{4a}$ and $R^{4b}$ are each alkyl (e.g., methyl), $R^2$, $R^{2'}$, $R^{4'}$, $R^5$, $R^{5'}$, $R^6$, $R^{6'}$, $R^8$, $R^9$, $R^{10}$, $R^{11}$ and $R^{12}$ are each hydrogen; J is $OR^{7o}$; $R^{7o}$ is alkyl (e.g., ethyl or t-butyl) and $R^{7l}$ is alkyl (e.g., methyl) or aminoalkyl (e.g., dialkylaminoalkyl, such as dimethylaminoethyl).

In one embodiment, X is $CR^{6'}R^6$, $R^4$ is $NR^{4a}R^{4b}$, $R^{4a}$ and $R^{4b}$ are each alkyl (e.g., methyl), $R^2$, $R^{2'}$, $R^3$, $R^{4'}$, $R^5$, $R^{5'}$, $R^6$, $R^{6'}$, $R^8$, $R^{10}$, $R^{11}$ and $R^{12}$ are each hydrogen; $R^9$ is amino; $R^{7l}$ is alkyl (e.g., methyl); J is $OR^{7o}$; $R^{7o}$ is alkyl (e.g., halogen substituted alkyl; such as fluorine substituted alkyl, for example, $CF_3CH_2-$; ethyl or t-butyl).

In another embodiment, X is $CR^{6'}R^6$, $R^4$ is $NR^{4a}R^{4b}$, $R^{4a}$ and $R^{4b}$ are each alkyl (e.g., methyl), $R^2$, $R^{2'}$, $R^3$, $R^{4'}$, $R^5$, $R^{5'}$, $R^6$, $R^{6'}$, $R^8$, $R^{10}$, $R^{11}$ and $R^{12}$ are each hydrogen; $R^9$ is aminoalkyl (e.g., t-butylaminomethyl); $R^{7o}$ is alkyl (e.g., ethyl); and $R^{7l}$ is alkyl (e.g., methyl).

In yet another embodiment, X is $CR^{6'}R^6$, $R^4$ is $NR^{4a}R^{4b}$, $R^{4a}$ and $R^{4b}$ are each alkyl (e.g., methyl), $R^2$, $R^{2'}$, $R^3$, $R^{4'}$, $R^5$, $R^{5'}$, $R^6$, $R^{6'}$, $R^8$, $R^9$, $R^{10}$, $R^{11}$ and $R^{12}$ are each hydrogen; J is $NR^{7m}R^{7n}$; $R^{7l}$ and $R^{7m}$) are each hydrogen and $R^{7n}$ is alkyl (e.g., t-butyl).

In a further embodiment, X is $CR^{6'}R^6$, $R^4$ is $NR^{4a}R^{4b}$, $R^{4a}$ and $R^{4b}$ are each alkyl (e.g., methyl), $R^2$, $R^{2'}$, $R^3$, $R^{4'}$, $R^5$, $R^{5'}$, $R^6$, $R^{6'}$, $R^{7l}$, $R^8$, $R^9$, $R^{11}$, and $R^{12}$ are each hydrogen; J is heteroaryl (e.g., pyrrolyl).

Examples of substituted tetracycline compounds of formula II include, for example:

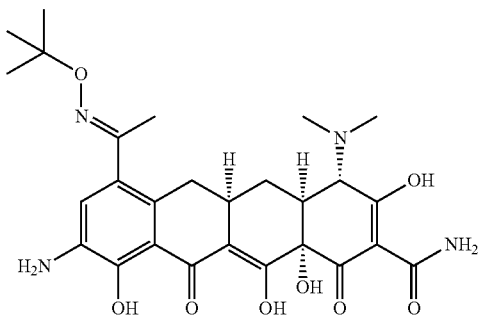

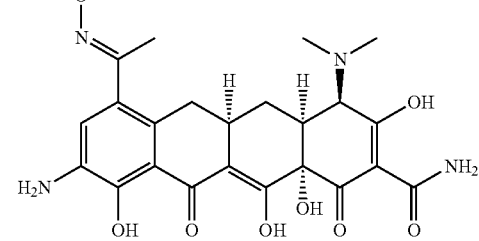

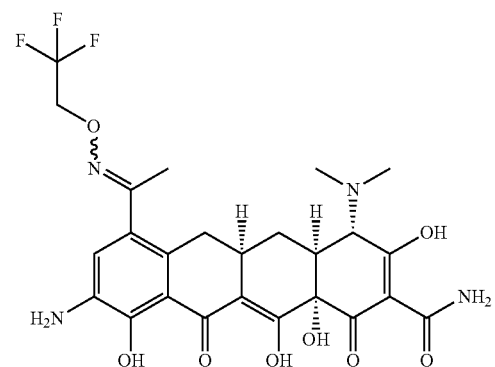
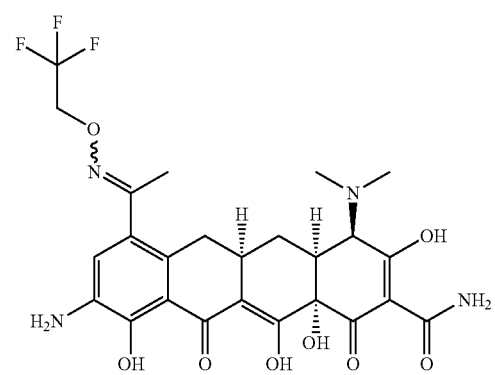
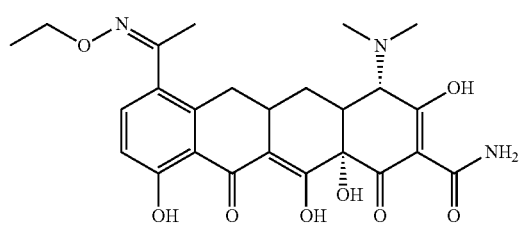 [SMILES: CCO/N=C(/C)c1ccc(O)c2c1CC1CC3[C@H](N(C)C)C(O)=C(C(N)=O)C(=O)[C@@]3(O)C(O)=C1C2=O]
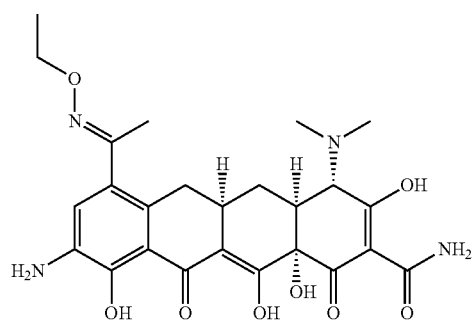
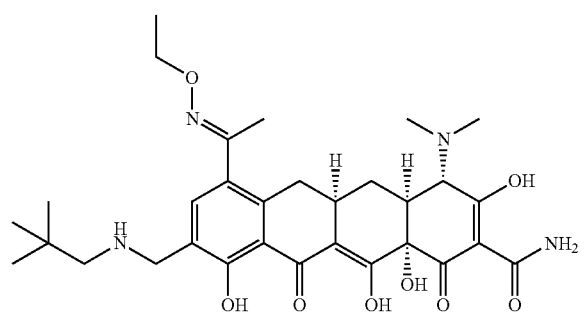
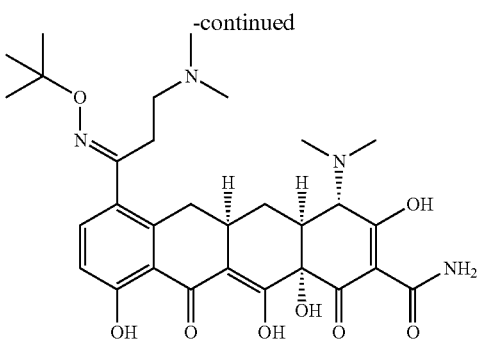
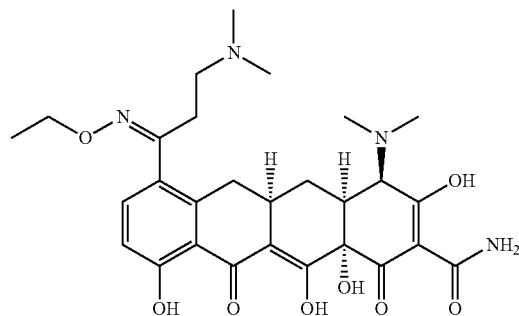
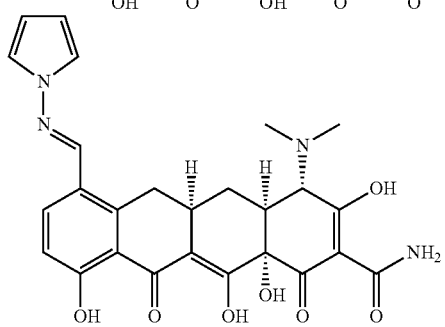
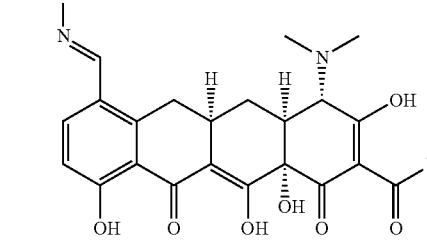
and pharmaceutically acceptable salts thereof.
In another embodiment, the substituted tetracycline compound of the invention is a compound of formula III:
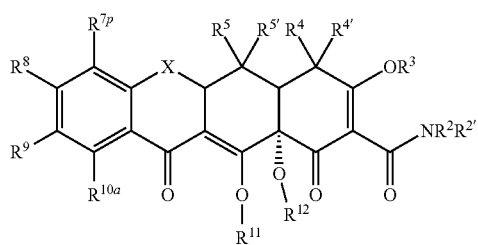

wherein

X is CHC(R$^{13}$Y'Y), CR$^6$R$^{6'}$, C=CR$^{6'}$R$^6$, S, NR$^6$, or O;

R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{11}$ and R$^{12}$ are each hydrogen or a prodrug moiety;

R$^4$ is NR$^{4a}$R$^{4b}$, alkyl, alkenyl, alkynyl, hydroxyl, halogen, or hydrogen;

R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^{7p}$ is hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;

Z is CR$^{9d}$R$^{9e}$, S, NR$^{9b}$ or O;

Z' is O, S, or NR$^{9f}$;

R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^{10a}$ is hydrogen;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is CR$^{6'}$R$^6$, R$^4$ may be NR$^{4a}$R$^{4b}$, R$^{4a}$ and R$^{4b}$ may each be alkyl (e.g., methyl), R$^2$, R$^{2'}$, R$^3$, R$^{4'}$, R$^5$, R$^{5'}$, R$^6$, R$^{6'}$, R$^8$, R$^9$, R$^{10a}$, R$^{11}$ and R$^{12}$ may each be hydrogen and R$^{7p}$ may be alkylamino (e.g., dialkylamino, such as dimethylamino), aminoalkyl (e.g., piperidinyl, such as 4-methylpiperidinyl), acyl, or aryl (e.g., heteroaryl, such as pyrimidine or pyrazine).

Examples of substituted tetracycline compounds of formula III include, for example:

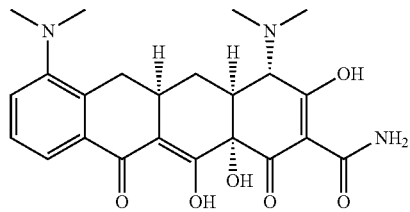 [SMILES: CN(C)c1cccc2c1C[C@H]1C[C@H]3[C@H](N(C)C)C(O)=C(C(N)=O)C(=O)[C@@]3(O)C(O)=C1C2=O]

-continued

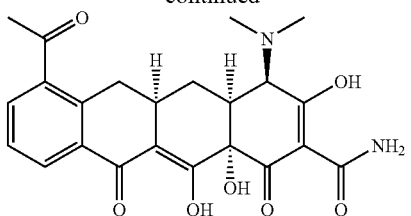

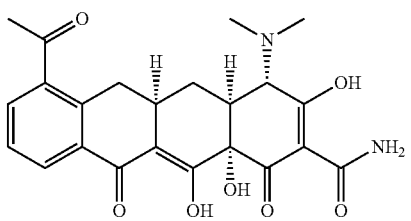 [SMILES: CC(=O)c1cccc2c1C[C@H]1C[C@H]3[C@H](N(C)C)C(O)=C(C(N)=O)C(=O)[C@@]3(O)C(O)=C1C2=O]

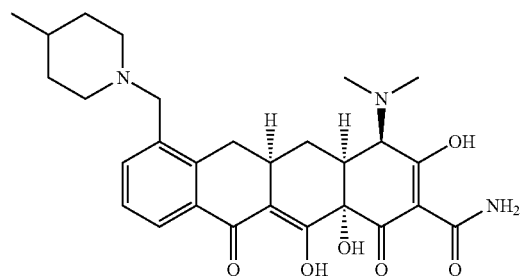 [SMILES: CC1CCN(Cc2cccc3c2C[C@H]2C[C@H]4[C@@H](N(C)C)C(O)=C(C(N)=O)C(=O)[C@@]4(O)C(O)=C2C3=O)CC1]

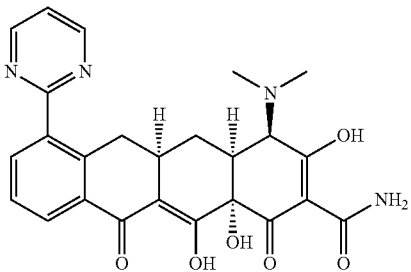 [SMILES: CN(C)[C@H]1C(O)=C(C(N)=O)C(=O)[C@@]2(O)C(O)=C3C(=O)c4cccc(-c5ncccn5)c4C[C@H]3C[C@@H]12]

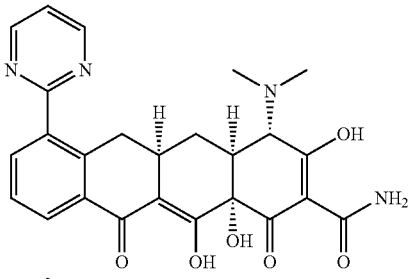

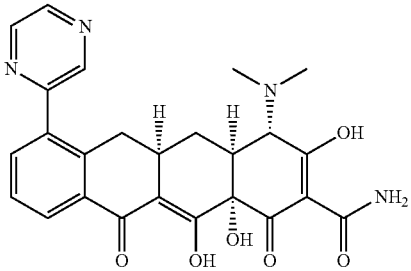

and pharmaceutically acceptable salts thereof.

In another embodiment, the substituted tetracycline compound of the invention is a compound of formula IV:

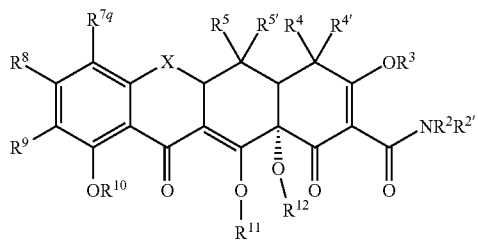

(IV)

wherein

X is CHC(R$^{13}$Y'Y), CR$^{6'}$R$^6$, C=CR$^{6'}$R$^6$, S, NR$^6$, or O;

R$^2$, R$^{2'}$, R$^{4'}$, R$^{4a}$ and R$^{4b'}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a prodrug moiety;

R$^4$ is NR$^{4a}$R$^{4b}$, alkyl, alkenyl, alkynyl, hydroxyl, halogen, or hydrogen;

R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R$^{7q}$ is heteroaryl;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;

Z is CR$^{9d}$R$^{9e}$, S, NR$^{9b}$ or O;

Z' is O, S, or NR$^{9f}$;

R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is CR$^{6'}$R$^6$, R$^4$ may be NR$^{4a}$R$^{4b}$, R$^{4a}$ and R$^{4b}$ may each be alkyl (e.g., methyl), R$^2$, R$^{2'}$, R$^3$, R$^{4'}$, R$^5$, R$^{5'}$, R$^6$, R$^{6'}$, R$^8$, R$^9$, R$^{10}$, R$^{11}$ and R$^{12}$ may each be hydrogen, and R$^{7p}$ is heteroaryl (e.g., oxazolyl, isoxazolyl, thiazolyl or pyrrolyl).

Examples of substituted tetracycline compounds of formula IV include, for example:

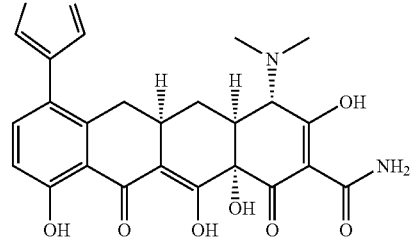
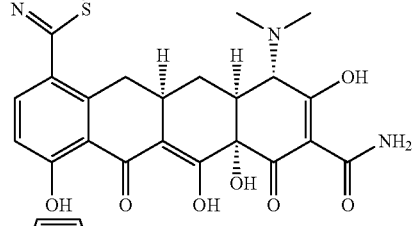
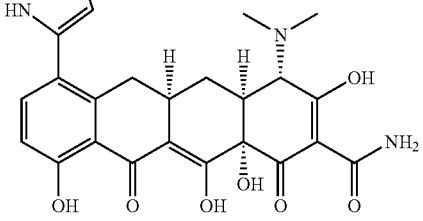
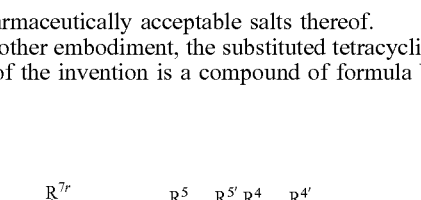

and pharmaceutically acceptable salts thereof.

In another embodiment, the substituted tetracycline compound of the invention is a compound of formula V:

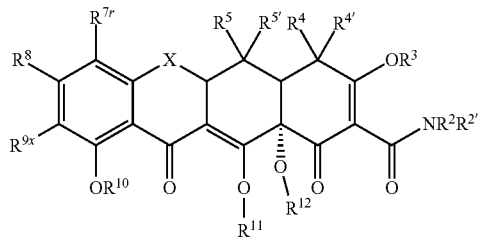

(V)

wherein

X is CHC(R$^{13}$Y'Y), CR$^{6'}$R$^6$, C=CR$^{6'}$R$^6$, S, NR$^6$, or O;

R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^3$, R$^{10}$, R$^{11}$ and R$^{12}$ are each hydrogen or a prodrug moiety;

R$^4$ is NR$^{4a}$R$^{4b}$, alkyl, alkenyl, alkynyl, hydroxyl, halogen, or hydrogen;

R⁵ and R⁵' are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7r}$ is hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;

R⁸ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{9x}$ is CN, $CR^{9g}NR^{9h}$ or $CR^{9i}R^{9j}NR^{9k}R^{9l}$;

$R^{9g}$, $R^{9h}$, $R^{9i}$, $R^{9j}$, $R^{9k}$ and $R^{9l}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;

R¹³ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6'}R^6$, R⁴ may be $NR^{4a}R^{4b}$, $R^{4a}$ and $R^{4b}$ may each be alkyl (e.g., methyl), R², R²', R³, R⁴', R⁵, R⁵', R⁶, R⁶', R⁸, R¹⁰, R¹¹ and R¹² are each hydrogen, $R^{7r}$ may be alkylamino (e.g., dialkylamino, such as dimethylamino) and $R^{9x}$ is CN. Alternatively, $R^{9x}$ may be $CR^{9g}NR^{9h}$, $R^{9g}$ is hydrogen and $R^{9h}$ is alkoxy (e.g., methoxy). In another embodiment, $R^{9x}$ may be $CR^{9i}R^{9j}NR^{9k}R^{9l}$, $R^{9i}$ and $R^{9j}$ are each hydrogen, $R^{9k}$ may be alkyl (e.g., methyl) and $R^{9l}$ is alkoxy (e.g., methoxy). In yet another embodiment, $R^{9k}$ is hydrogen and $R^{9l}$ is alkoxy (e.g., methoxy).

In a further embodiment, X is $CR^{6'}R^6$, R⁴ may be $NR^{4a}R^{4b}$, $R^{4a}$ and $R^{4b}$ may each be alkyl (e.g., methyl), R², R²', R³, R⁴', R⁵, R⁵', R⁶, R⁶', R⁸, R¹⁰, R¹¹ and R¹² are each hydrogen, $R^{7r}$ is hydrogen, $R^{9f}$ is $CR^{9i}R^{9j}NR^{9k}R^{9l}$; $R^{9i}$, $R^{9j}$ and $R^{9k}$ are each hydrogen; and $R^{9l}$ is alkoxy (e.g., ethoxy).

In yet another embodiment, In a further embodiment, X is $CR^{6'}R^6$, R⁴ may be $NR^{4a}R^{4b}$, R², R³, R⁴, R⁵, R⁵', R⁶, R⁶', R⁸, R⁹, R¹⁰, R¹¹ and R¹² are each hydrogen, $R^{7r}$ is hydrogen, $R^{9x}$ is $CR^{9i}R^{9j}NR^{9k}R^{9l}$; $R^{9i}$ and $R^{9j}$ are each hydrogen and $R^{9k}$ is alkyl (e.g., methyl) and $R^{9l}$ is alkoxyl (e.g., methoxy).

Examples of substituted tetracycline compounds of formula V include, for example:

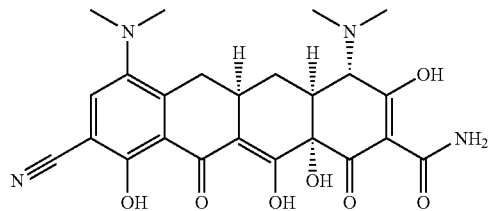

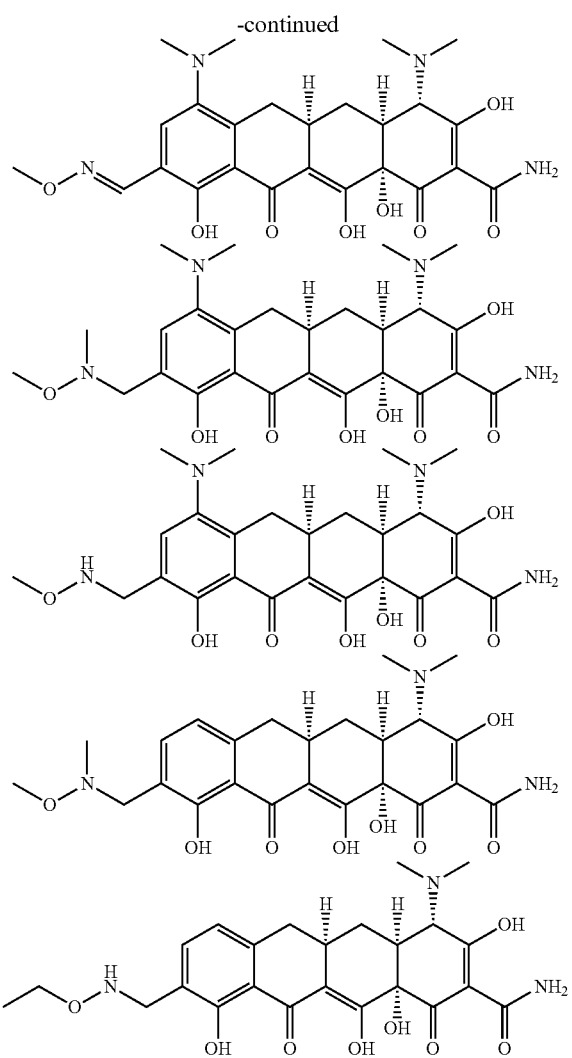

and pharmaceutically acceptable salts thereof.

In yet another embodiment, a substituted tetracycline compound of the invention may be a compound of formula VI:

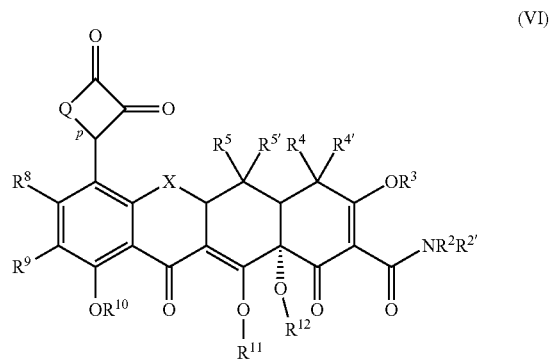

(VI)

wherein

X is $CHC(R^{13}Y'Y)$, $CR^{6'}R^6$, $C{=}CR^{6'}R^6$, S, NR⁶, or O;

p is a single bond or a double bond;

Q is $CR^{7s}$ when p is a double bond or Q is $CR^{7s'}R^{s''}$ when p is a single bond;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a prodrug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7S}$, $R^{7s'}$ and $R^{7s''}$ are each hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or $-(CH_2)_{0-3}(NR^{9c})_{0-1}C(=Z')ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6'}R^6$, $R^4$ is $NR^{4a}R^{4b}$, $R^{4a}$ and $R^{4b}$ are each alkyl (e.g., methyl) and $R^2$, $R^{2'}$, $R^3$, $R^{4'}$, $R^5$, $R^{5'}$, $R^6$, $R^{6'}$, $R^8$, $R^9$, $R^{10}$, $R^{11}$ and $R^{12}$ are each hydrogen. In another embodiment, p is a double bond and Q is $CR^{7s}$. In a further embodiment, $R^{7s}$ is amino, alkylamino (e.g., methylamino) or dialkylamino (e.g., dimethylamino).

Examples of substituted tetracycline compounds of formula VI include, for example:

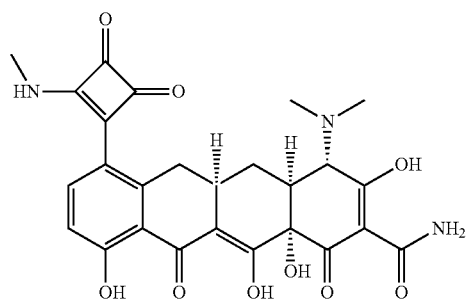

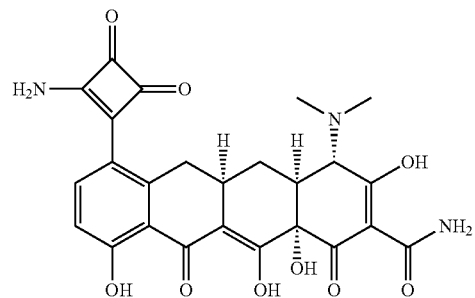

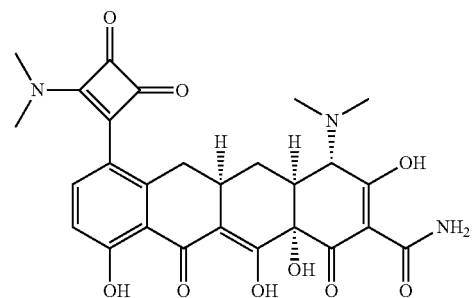

and pharmaceutically acceptable salts thereof.

The tetracycline compounds of this invention can be synthesized using the methods described in the Schemes and/or by other techniques known to those of ordinary skill in the art. The substituted tetracycline compounds of the invention can be synthesized using the methods described in the following schemes and by using art recognized techniques. All novel substituted tetracycline compounds described herein are included in the invention as compounds.

In Scheme 1, a general synthetic scheme for synthesizing 7-substituted tetracyclines is shown. A palladium catalyzed coupling of an iodosancycline (1) is performed to form a 7-substituted aldehyde intermediate (2). The aldehyde intermediate is reduced in the presence of a hydroxylamine to give the desired product (3).

Scheme 1

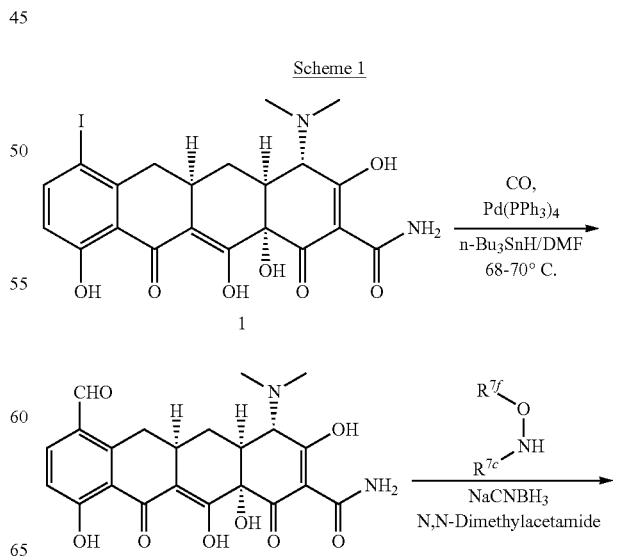

-continued

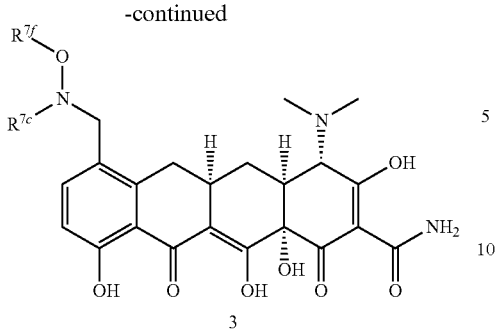
3

7- and 9-substituted tetracycline compounds may be synthesized by reacting the 7-iodo-9-aminoalkyl sancycline derivative (4) with trimethylsilylethyne in the presence of a palladium catalyst to yield a 7-substituted alkynyl intermediate. Subsequent acid hydrolysis yields the 7-acyl intermediate (5). Further derivitization of the 9-position may be accomplished by reductive alkylation of the amino group with t-butyl aldehyde, hydrogen and palladium on carbon to form compound 6, which can then be reacted with a primary hydroxylamine to form the oxime 7.

Scheme 2

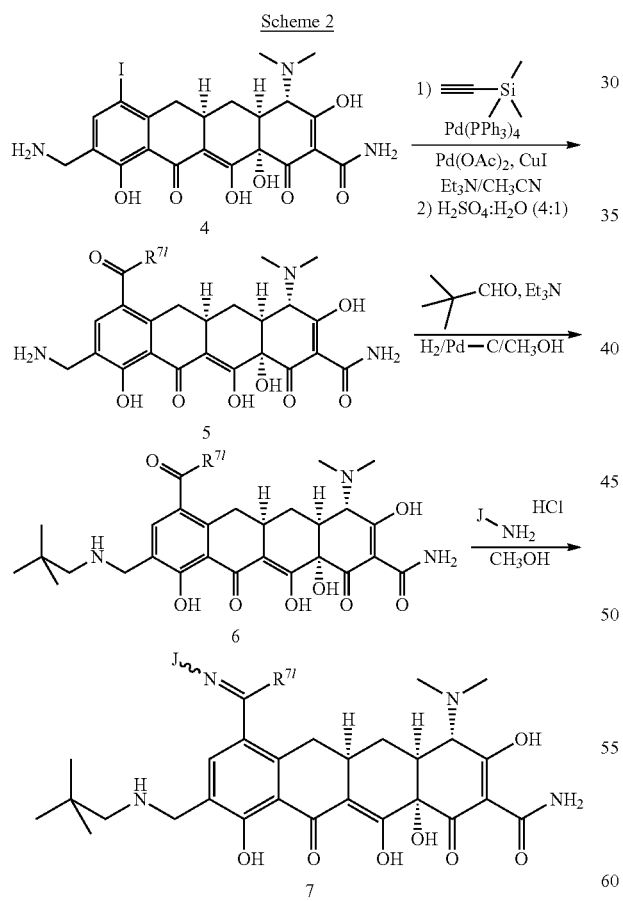

7- and 9-substituted tetracycline compounds may also be prepared as shown in Scheme 3. Beginning with a 7-iodo-9-nitro substituted sancycline derivative (8), a Hiyama coupling followed by acid hydrolysis yields a 7-acyl-9-nitro intermediate (9). The nitro moiety may then be reduced to the amino group by hydrogen gas in the presence of a palladium catalyst (10). Reaction of the acyl group with a primary hydroxylamine provides the product 11.

Scheme 3

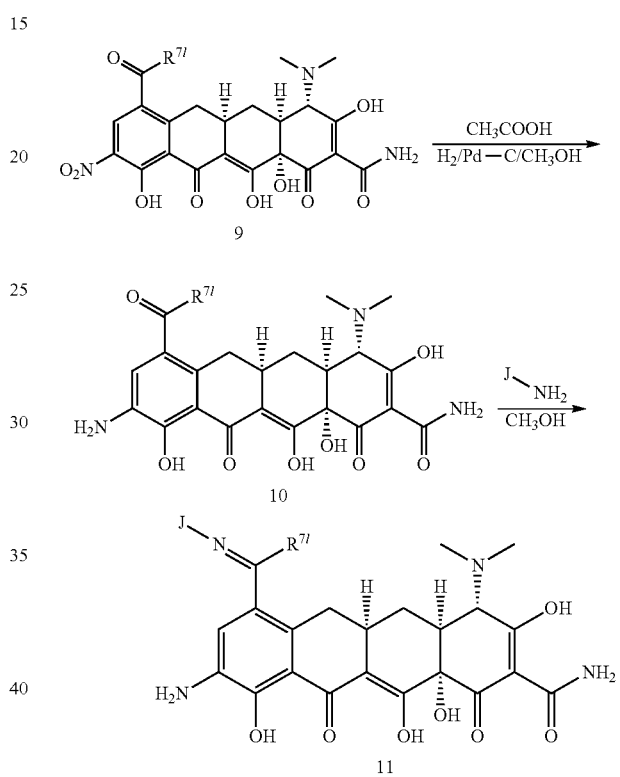

Scheme 4 also provides a method for synthesizing 7-substituted tetracyclines. As described above, a palladium catalyzed carbonylation of an iodosancycline (1) is performed to form a 7-substituted aldehyde intermediate (2). The aldehyde intermediate is reduced in the presence of a hydroxylamine to give compound 12, which may then be reacted with formaldehyde and triethylamine, followed by reduction to give the desired product (3).

Scheme 4

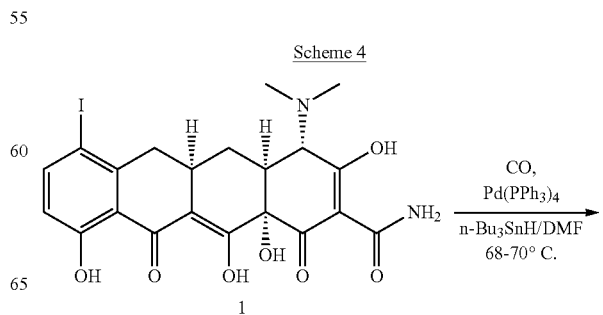

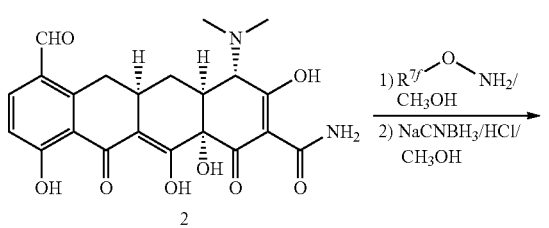

2

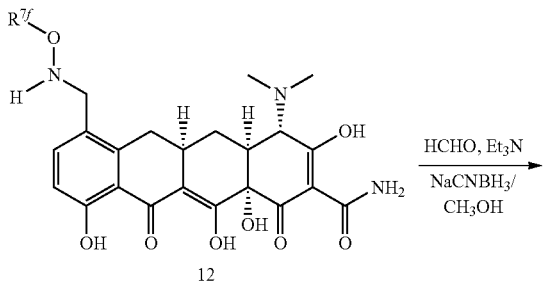

12

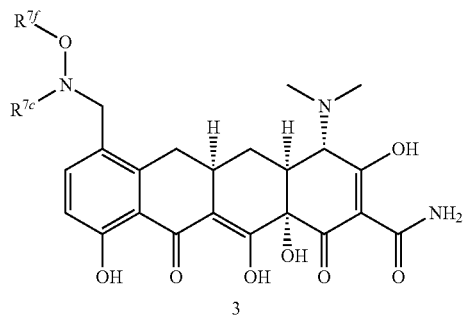

3

Scheme 5 details the synthesis of substituted tetracyclines with hydroxy in the 10-position. A 7-substituted tetracycline compound may be reacted with N-(5-chloro-2-pyridyl)bis(trifluoromethanesulfonimide) to form a trifluoromethane substituted intermediate (14), which can then be reacted with ammonium formate in the presence of a palladium catalyst to form the desired product (15).

Scheme 5

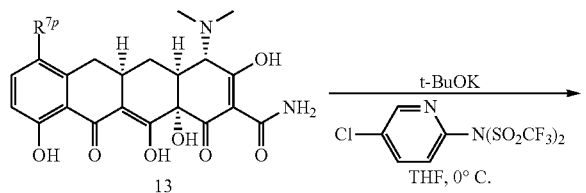

13

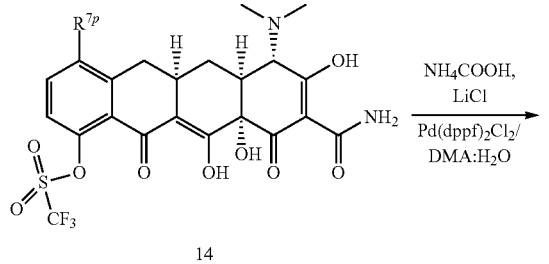

14

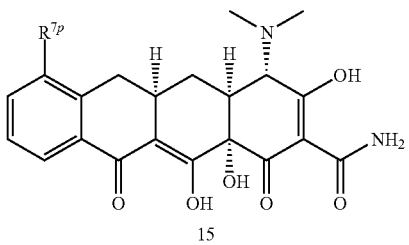

15

Scheme 6 outlines the general synthesis of 7-substituted tetracyclines. A 7-iodo sancycline derivative (1) may undergo a Stille coupling or a Suzuki coupling by reacting with an alkyl tin derivative or a boronic acid derivative in the presence of a palladium catalyst to form the desired product (16).

Scheme 6

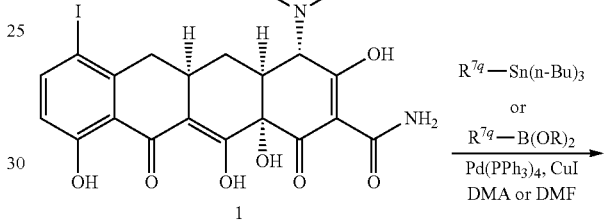

1

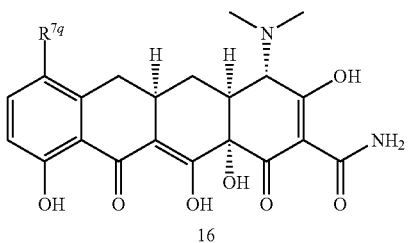

16

The 7-substituted oxime derivatives may also be prepared as shown in Scheme 7. An 7-iodo sancycline derivative (1) can be reacted with a substituted alkyne in the presence of palladium to synthesize the alkynyl derivative 17. Compound 17 may be converted to the acyl substituted compound 18 by any technique known in the art. The desired oxime product 19 can be obtained by reacting the acyl moiety with a primary hydroxylamine.

Scheme 7

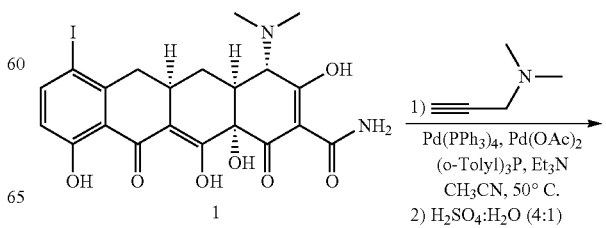

1

-continued

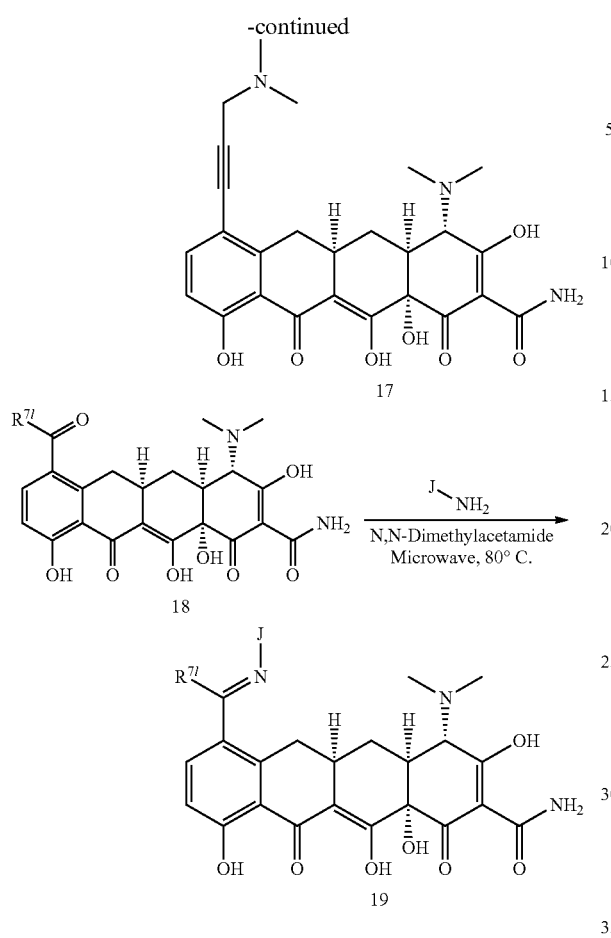

Scheme 8 is a general synthetic scheme showing the synthesis of 7-substituted hydrazone compounds. A 7-substituted aldehyde tetracycline derivative, prepared as described above in Scheme 4, is combined with a primary hydrazone to form the desired product 20.

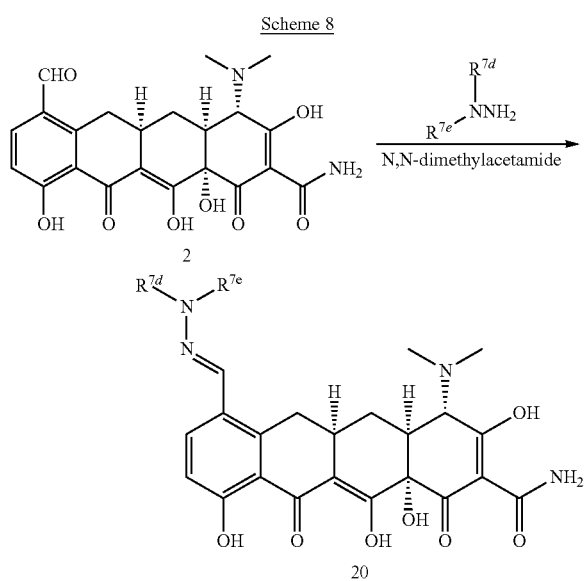

7-substituted hydrazines may also be synthesized as shown in Scheme 9. Starting with compound 2, synthesized as described in Scheme 4 above, may be reacted with a secondary hydrazine in the presence of a reducing agent to form compound 21.

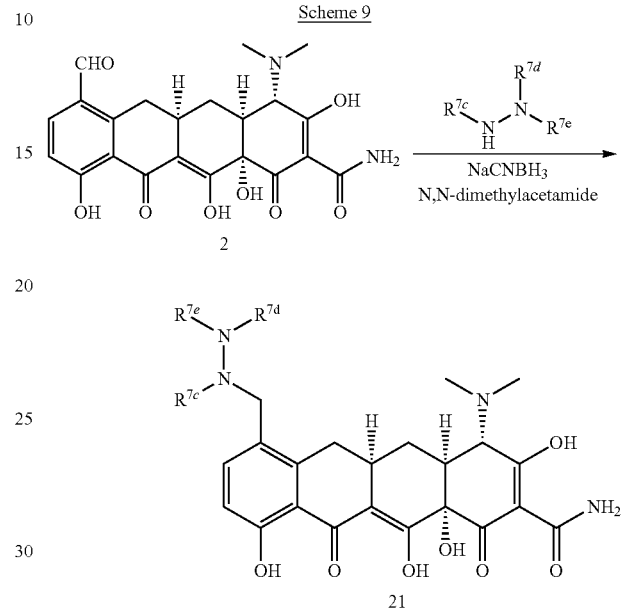

Scheme 10 further depicts a method of synthesizing a 7-substituted aminoalkyl tetracycline compound. Compound 2 is reacted with a primary amine in the presence of a reducing agent to form the secondary amine intermediate (22), which is then mixed with an acid chloride to form compound 23.

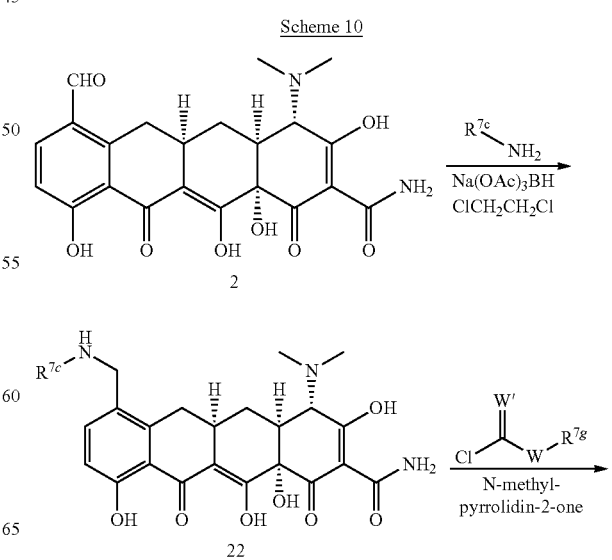

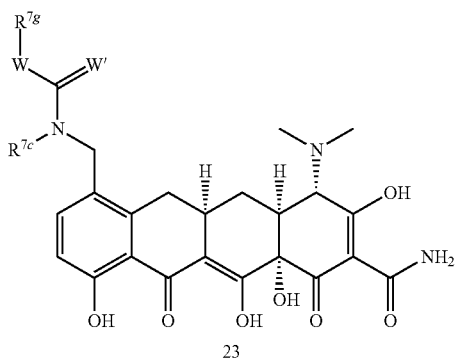

Scheme 11 describes a general method for preparing 9-substituted aminoalkyl substituted tetracycline compounds. Compound 24 may be reacted directly with a secondary amine to form compounds similar to 26. Alternatively, compound 24 may be mixed with a primary amine to yield the substituted imine 25, which may be further reduced to produce the aminoalkyl compound 26.

7-substituted tetracycline may also be prepared as shown in Scheme 12. Starting again with compound 2, reductive alkylation with a dioxalanyl secondary amine yields the intermediate 27. Subsequently exposing 27 to acidic conditions removes the protecting group to form intermediate 28, which may then be reacted with a primary amine to form product 29.

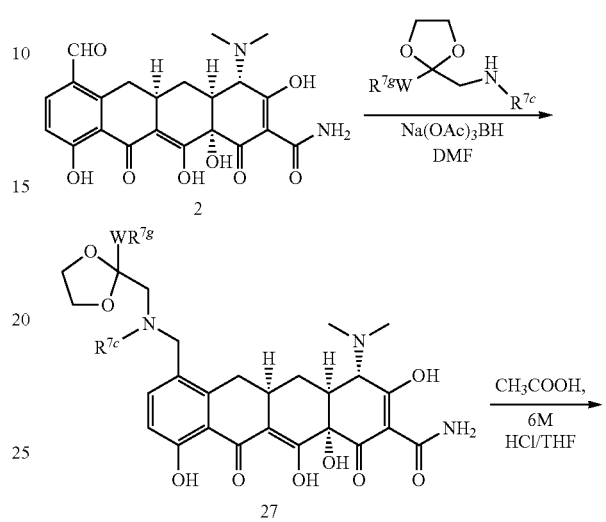

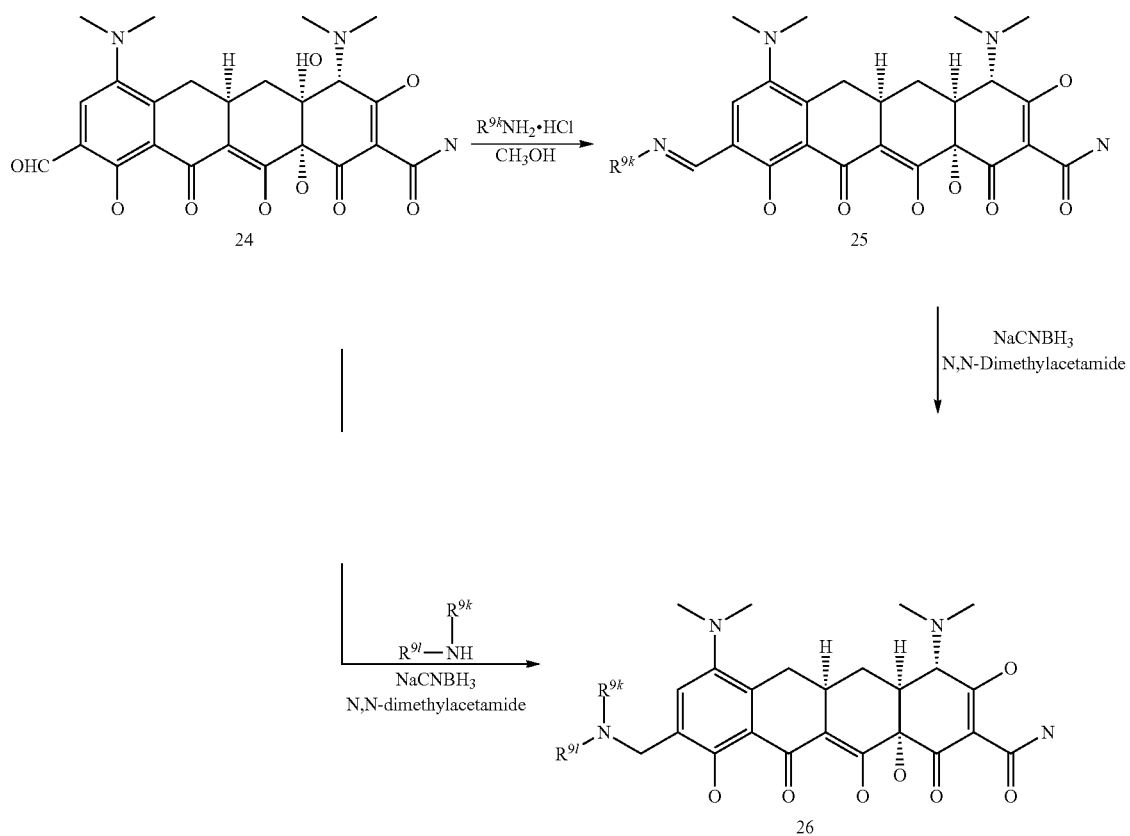

-continued

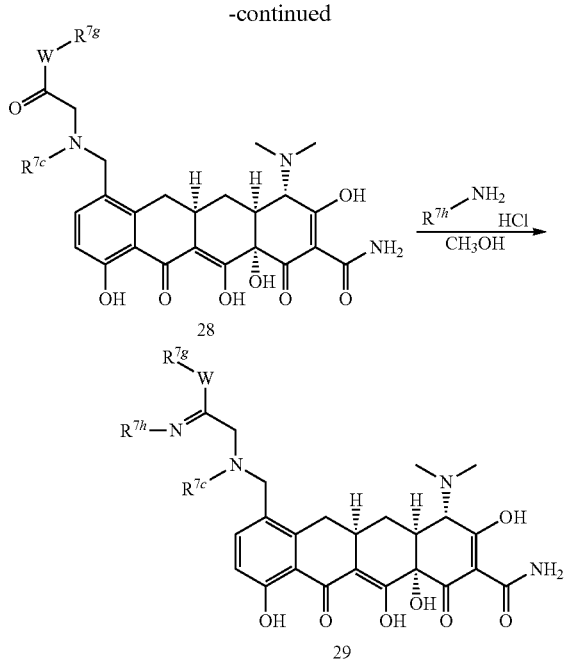

Schemes 13 and 14 illustrate the general synthesis of cyclobutene 7-substituted tetracycline compounds. Beginning with 30, tin regeant 31 is synthesized by reacting 30 with a trimethylsilyl substituted alkyltin derivative.

Scheme 13

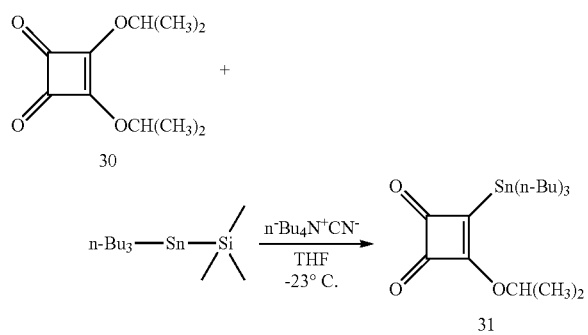

Scheme 14 continues to show the synthesis of cyclobutenedione 7-substituted tetracycline compounds, by reacting building block 31 with 7-iodo substituted sancycline (1) in a Stille coupling reaction to form 32. The amino substitution of product 33 is accomplished by reacting 32 with a primary amine in methanol.

Scheme 14

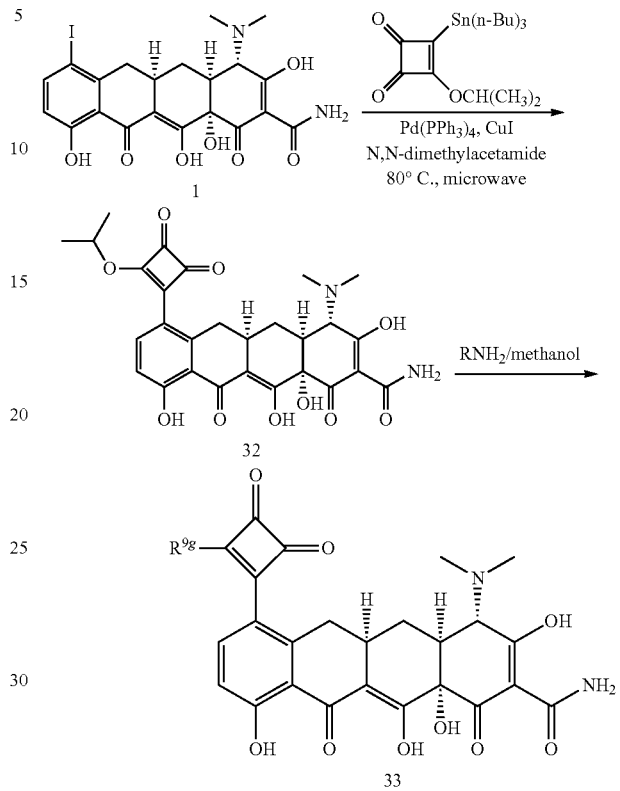

Scheme 15 illustrates the general synthesis of 9-substituted aminoalkyl substituted tetracycline compounds. A 7-bromo-9-formyl substituted tetracycline 34 may be reacted with a primary amine to yield the 9-substituted imino derivative 35. This intermediate may be exposed to a reducing agent (e.g., sodium cyanoborohydride) to yield the 7-bromo-9-aminoalkyl substituted compound 36. Alternatively, compound 36 may be prepared by reacting the starting material 34 with a reducing agent (e.g., sodium cyanoborohydride) in the presence of a secondary amine. The 7-position may be dehalogenated in the presence of ammonium formate, indium trichloride and a palladium catalyst to give the desired product 37.

Scheme 15

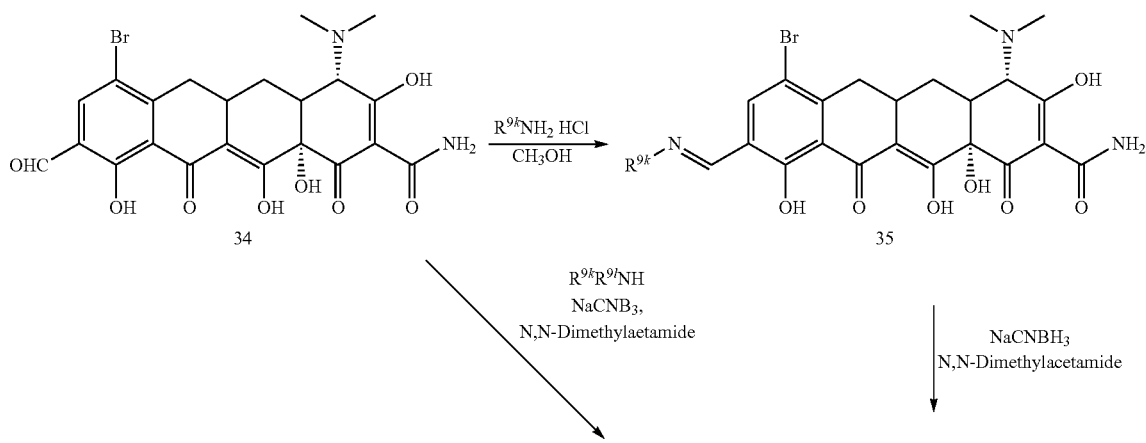

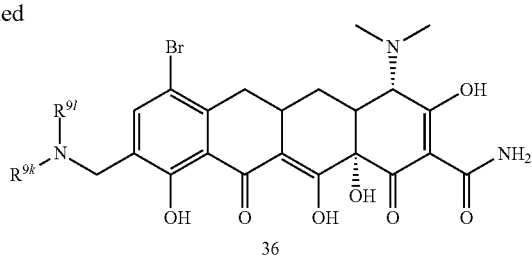

36

Ammonium Formate
Pd(dppf)₂CH₂Cl₂,
InCl₃, NMP

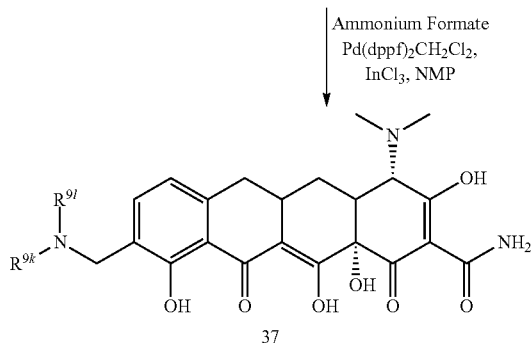

37

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclobutyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups.

Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group.

The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with and —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts," *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (+, acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

In another further embodiment, the substituted tetracycline compound is administered in combination with a second agent.

The language "in combination with" a second agent includes co-administration of the tetracycline compound with the second agent, administration of the tetracycline compound first, followed by the second agent and administration of the second agent, followed by the tetracycline compound. The second agent may be any agent which is known in the art to treat, prevent, or reduce the symptoms of a skin disorder. Furthermore, the second agent may be any agent of benefit to the subject when administered in combination with the administration of an tetracycline compound.

In another embodiment, the invention pertains to pharmaceutical compositions comprising an effective amount of a substituted tetracycline compound of the invention for the treatment of an inflammatory skin disorder and a pharmaceutically acceptable carrier.

The language "pharmaceutically acceptable carrier" includes substances capable of being coadministered with the tetracycline compound(s), and which allow both to perform their intended function, e.g., treat or prevent an inflammatory skin disorder. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, tetracycline compounds of the present invention may be administered topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats.

It will be appreciated that the actual preferred amounts of active compounds used in a given therapy will vary according to the specific compound being used, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g., 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a substituted tetracycline of the invention, for the preparation of a medicament. The medicament may include a pharmaceutically acceptable carrier and the tetracycline compound is an effective amount, e.g., an effective amount to treat an inflammatory skin disorder.

In one embodiment, the compounds of the invention are compounds of Table 2.

TABLE 2

| Compound Code | Compound |
|---|---|
| A | |
| B | |

TABLE 2-continued

| Compound Code | Compound |
|---|---|
| C | (structure) |
| D | (structure) |
| E | (structure) |
| F | (structure) |
| G | (structure) |
| H | (structure) |

TABLE 2-continued

| Compound Code | Compound |
|---|---|
| I | |
| J | |
| K | |
| L | |
| M | |

TABLE 2-continued

| Compound Code | Compound |
|---|---|
| N | |
| O | |
| P | |
| Q | |
| R | |

TABLE 2-continued
| Compound Code | Compound |
|---|---|
| S | 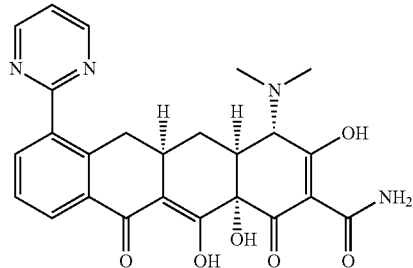 [SMILES: CN(C)[C@@H]1C(O)=C(C(N)=O)C(=O)[C@@]2(O)C(O)=C3C(=O)c4cccc(-c5ncccn5)c4C[C@H]3C[C@@H]12] |
| T | 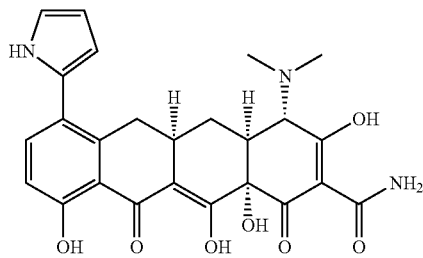 [SMILES: CN(C)[C@@H]1C(O)=C(C(N)=O)C(=O)[C@@]2(O)C(O)=C3C(=O)c4c(O)ccc(-c5ccc[nH]5)c4C[C@H]3C[C@@H]12] |
| U | 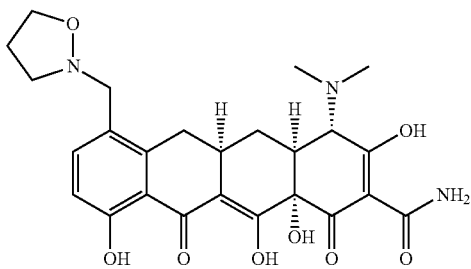 [SMILES: CN(C)[C@@H]1C(O)=C(C(N)=O)C(=O)[C@@]2(O)C(O)=C3C(=O)c4c(O)ccc(CN5CCCO5)c4C[C@H]3C[C@@H]12] |
| V | 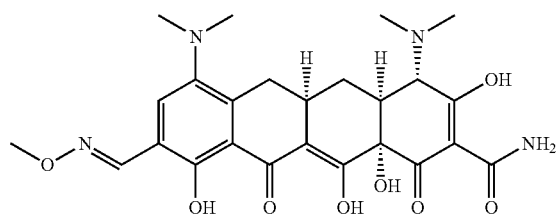 [SMILES: CO/N=C/c1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| W | 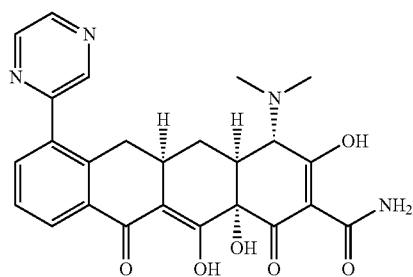 [SMILES: CN(C)[C@@H]1C(O)=C(C(N)=O)C(=O)[C@@]2(O)C(O)=C3C(=O)c4cccc(-c5cnccn5)c4C[C@H]3C[C@@H]12] |

TABLE 2-continued

| Compound Code | Compound |
|---|---|
| X | |
| Y | |
| Z | |
| AA | |
| AB | |

TABLE 2-continued

| Compound Code | Compound |
|---|---|
| AC | *(structure)* |
| AD | *(structure)* |
| AE | *(structure)* |
| AF | *(structure)* |

TABLE 2-continued
| Compound Code | Compound |
|---|---|
| AG | 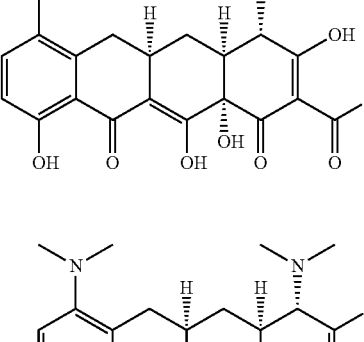 |
| AH | 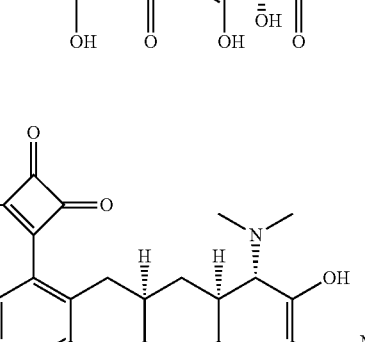 |
| AI | 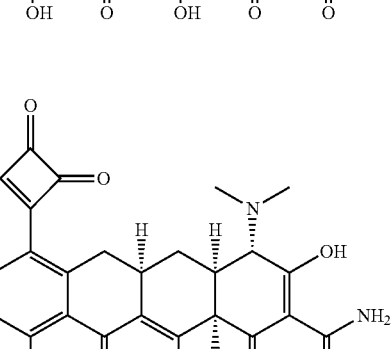 |
| AJ | 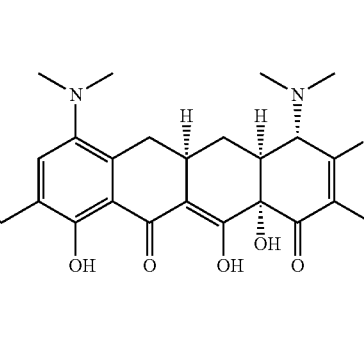 |
| AK | 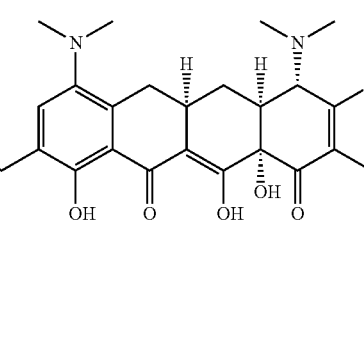 |

TABLE 2-continued

| Compound Code | Compound |
|---|---|
| AL | |
| AM | |
| AN | |
| AO | |
| AP | |

TABLE 2-continued
| Compound Code | Compound |
|---|---|
| AQ | 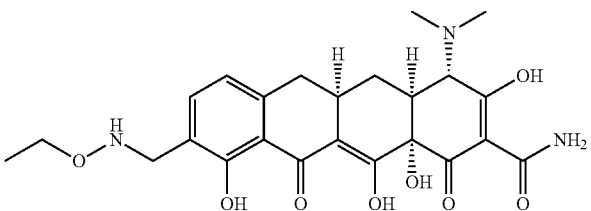 [SMILES: CCONCc1ccc2c(c1O)C(=O)C1=C(O)[C@]3(O)C(=O)C(C(N)=O)=C(O)[C@@H](N(C)C)[C@@H]3C[C@@H]1C2] |
| AR | 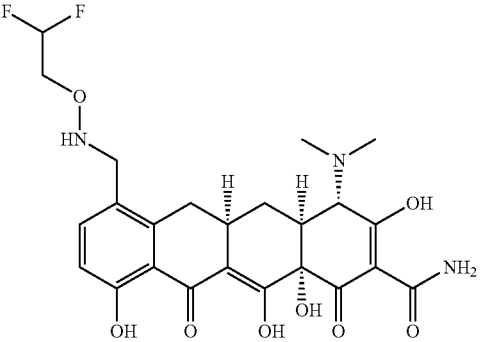 [SMILES: CN(C)[C@@H]1C(O)=C(C(N)=O)C(=O)[C@@]2(O)C(O)=C3C(=O)c4c(O)ccc(CNOCC(F)F)c4C[C@H]3C[C@@H]12] |
| AS | 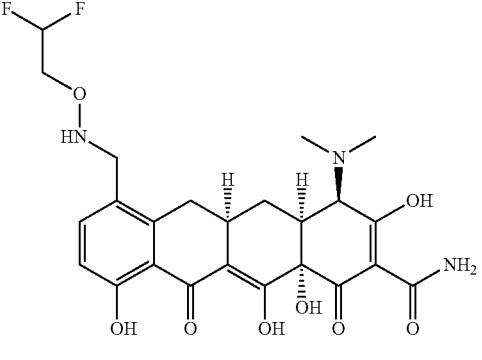 [SMILES: CN(C)[C@H]1C(O)=C(C(N)=O)C(=O)[C@@]2(O)C(O)=C3C(=O)c4c(O)ccc(CNOCC(F)F)c4C[C@H]3C[C@@H]12] |
| AT | 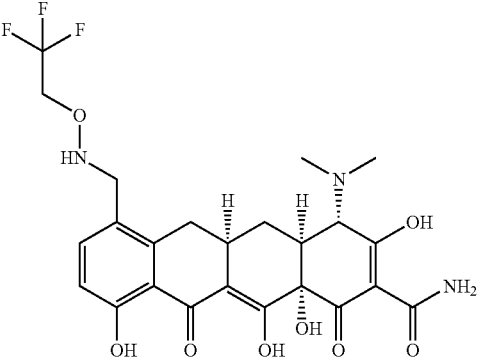 [SMILES: CN(C)[C@@H]1C(O)=C(C(N)=O)C(=O)[C@@]2(O)C(O)=C3C(=O)c4c(O)ccc(CNOCC(F)(F)F)c4C[C@H]3C[C@@H]12] |

TABLE 2-continued
| Compound Code | Compound |
|---|---|
| AU | 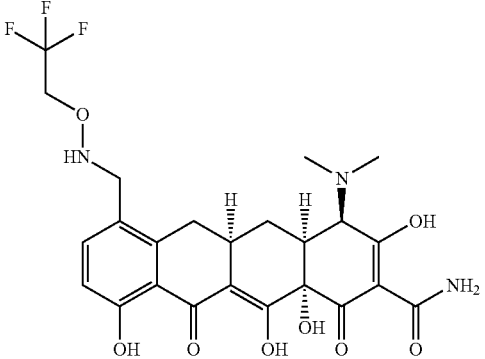 [SMILES: CN(C)[C@H]1C(O)=C(C(N)=O)C(=O)[C@@]2(O)C(O)=C3C(=O)c4c(O)ccc(CNOCC(F)(F)F)c4C[C@H]3C[C@@H]12] |
| AV | 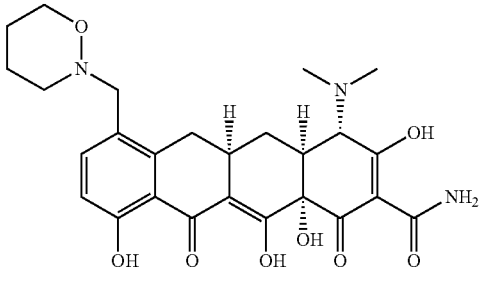 [SMILES: CN(C)[C@@H]1C(O)=C(C(N)=O)C(=O)[C@@]2(O)C(O)=C3C(=O)c4c(O)ccc(CN5CCCCO5)c4C[C@H]3C[C@@H]12] |
| AW | 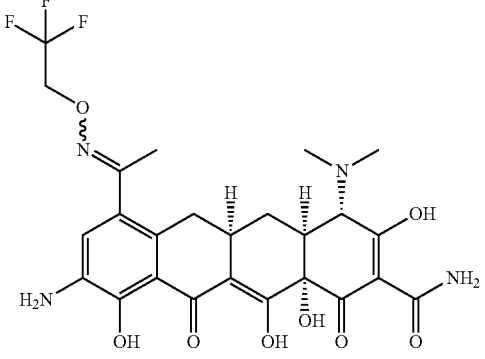 |
| AX | 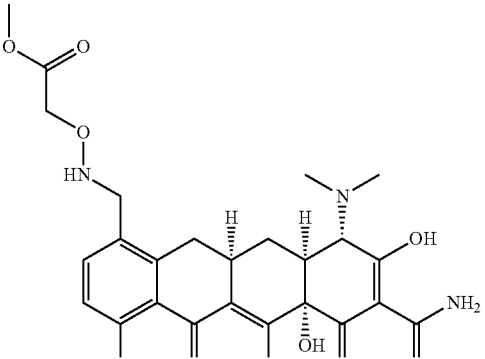 |

TABLE 2-continued
| Compound Code | Compound |
|---|---|
| AY | 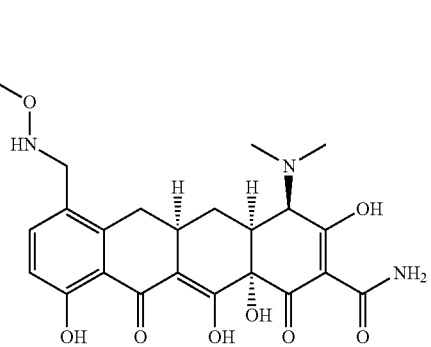 |
| AZ | 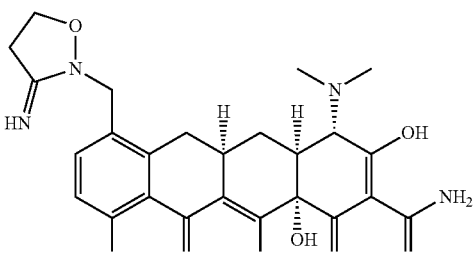 |
| BA | 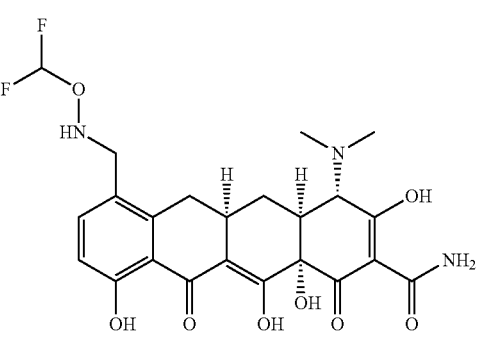 [SMILES: CN(C)[C@@H]1C(O)=C(C(N)=O)C(=O)[C@@]2(O)C(O)=C3C(=O)c4c(O)ccc(CNOC(F)F)c4C[C@H]3C[C@@H]12] |
| BB | 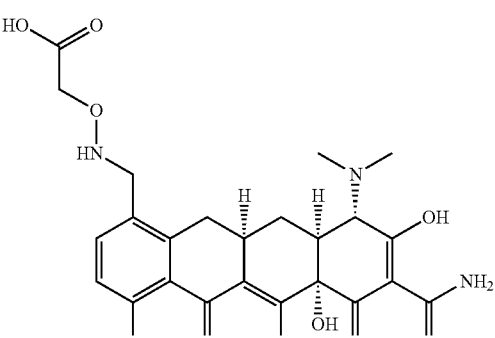 |

TABLE 2-continued

| Compound Code | Compound |
|---|---|
| BC | (tetracycline derivative with 7-position substituent: -CH₂-NH-O-CH₂-C(=O)-CH₃) |
| BD | (tetracycline derivative with 7-position substituent: -CH₂-NH-O-CH₂CH₂-O-CH₃) |
| BE | (tetracycline derivative with 7-position substituent: -C(CH₃)=N-O-CH₂-CF₃, and 9-NH₂) |
| BF | (tetracycline derivative with 7-position substituent: -CH₂-N(isoxazolidinyl)) |

EXEMPLIFICATION OF THE INVENTION

Example 1

Synthesis of Selected Compounds of the Invention (4S,4aS,5aR,12aS)-4-Dimethylamino-3,10,12,12a-tetrahydroxy-7-[methoxy-methyl-amino)-methyl]-1,11-dioxo-1,4,4a,5,5a,6,11,12a-octahydro-naphthacene-2-carboxylic acid amide (Compound P)

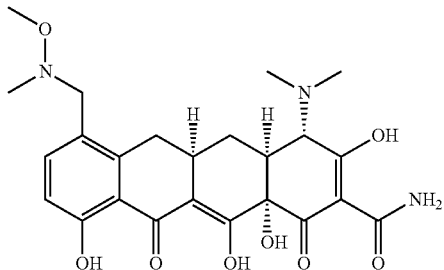 [SMILES: CON(C)Cc1ccc(O)c2c1C[C@H]1C[C@H]3[C@H](N(C)C)C(O)=C(C(N)=O)C(=O)[C@@]3(O)C(O)=C1C2=O]

A solution of 7-formylsancycline TFA salt (2.23 g) and N,O-dimethylhydroxylamine hydrochloride (780 mg) in N,N-dimethylacetamide (15 mL) was stirred for 10 minutes at room temperature under argon atmosphere. To this solution was added sodium cyanoborohydride (302 mg). The solution was stirred for 5 minutes and monitored by LC-MS. The reaction mixture was poured into diethyl ether, and the resulting precipitates were collected by filtration under vacuum. The crude product was purified by prep-HPLC using a C18 column (linear gradient 10-40% acetonitrile in 20 mM aqueous triethanolamine, pH 7.4). The prep-HPLC fractions were collected, and the organic solvent (acetonitrile) was evaporated in vacuo. The resulting aqueous solution was loaded onto a clean PDVB SPE column, washed with distilled water, then with a 0.1 M sodium acetate solution followed by distilled water. The product was eluted with 0.1% TFA in acetonitrile. After concentrating under vacuum, 565 mg was obtained as a TFA salt. The TFA salt was converted to the hydrochloride salt by adding methanolic HCl followed by in vacuo evaporation. This process was repeated twice to give a yellow solid: MS (Mz+1=488). $^1$H NMR (300 MHz, CD$_3$OD) δ 7.46 (d, 1H, J=8.6 Hz), 6.81 (d, 1H, J=8.6 Hz), 4.09 (d, 1H, J=1.0 Hz), 3.79 (d, 1H, J=13.1 Hz), 3.73 (d, 1H, J=13.1 Hz), 3.36 (m, 1H), 3.27 (s, 3H), 3.08-2.95 (8H), 2.61 (s, 3H), 2.38 (t, 1H, J=14.8), 2.22 (m, 1H), 1.64 (m, 1H). Compounds Y, U and AV were also prepared in a similar manner and compound BF may also be prepared in a similar manner.

(4S,4aS,5aR,12aS)-4-Dimethylamino-9-[(2,2-dimethyl-propylamino)-methyl]-7-(1-ethoxyimino-ethyl)-3,10,12,12a-tetrahydroxy-1,11-dioxo-1,4,4a,5,5a,6,11,12a-octahydro-naphthacene-2-carboxylic acid amide (Compound N)

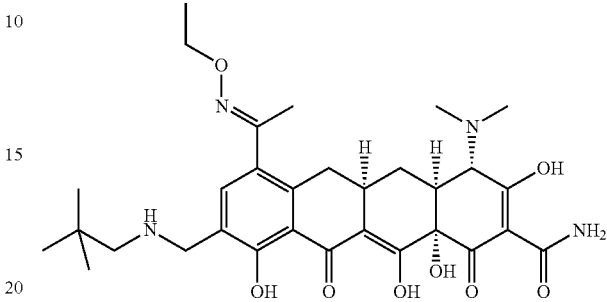

A mixture of 7-iodo-9-aminomethylsancycline (3.26 mmol), Pd(PPh$_3$)$_4$ (0.326 mmol), Pd(OAc)$_2$ (0.326 mmol), CuI (0.326 mmol) in acetonitrile (50 mL) and N,N-dimethylacetamide (8 mL) was purged with argon. While under argon atmosphere, triethylamine (16.25 mmol) and trimethylacetylene (4.9 mmol) were added and the reaction mixture was stirred for 4 hours at 50-60° C. The solvent was partially evaporated and the crude intermediate was cooled with an ice-bath and sulfuric acid solution (cone H$_2$SO$_4$: H$_2$O, 4/1, 25 mL) was added slowly and stirred for 5 minutes. The reaction mixture was then slowly poured into 1.2 L of water and filtered through celite pad. The filtrate was purified using short DVB column to give the intermediate 7-acetyl-9-aminomethylsancycline.

To a solution of 7-acetyl-9-aminomethylsancycline (1 mmol) in methanol (20 mL) was added triethylamine (0.7 mL). To the resulting suspension was added trimethylacetaldehyde (7.37 mmol) and the mixture was stirred for 20 minutes. Palladium on carbon (5%, 53% water, 300 mg) was added and the reaction mixture was stirred overnight under H$_2$ atmosphere at 20 psi. Excess trimethylacetaldehyde (3.7 mmol), Pd—C (150 mg) and triethylamine (0.2 mL) were then added and stirred for an additional 6 hours. The reaction mixture was then filtered through celite and the solvent was evaporated reduced. The crude product was purified by prep-HPLC using C18 column (linear gradient 5-32% acetonitrile in water with 0.1% TFA) to give 7-acetyl-9-(2,2-dimethylpropyl-amino)-methyl-sancycline.

A solution of 7-acetyl-9-[(2,2-dimethylpropylamino)-methyl]-sancycline (0.383 mmol) and O-ethylhydroxylamine hydrochloride (2.30 mmol) in methanol (15 mL) was stirred overnight. The solvent was evaporated and purified by prep-HPLC using C18 column (linear gradient 15-30% acetonitrile in water with 0.1% TFA) to give a yellow solid: MS (Mz+1=599); $^1$H NMR (300 MHz, CD$_3$OD) δ 7.60 (s, 1H), 4.33 (s, 2H), 5.06 (m, 2H), 4.16 (2H, q, J=7.0 Hz), 4.08 (s, 1H), 3.11-2.90 (11H), 2.52 (m, 1H), 2.18 (m, 1H), 2.15 (s, 3H), 1.28 (3H, t, J=7.0 Hz), 1.06 (s, 9H).

(4S,4aS,5aR,12aS)-9-Amino-7-(1-tert-butoxyimino-ethyl)-4-dimethylamino-3,10,12,12a-tetrahydroxy-1,11-dioxo-1,4,4a,5,5a,6,11,12a-octahydro-naphthacene-2-carboxylic acid amide (Compound Q)

(4S,4aS,5aR,12aS)-9-Amino-4-dimethylamino-3,10,12,12a-tetrahydroxy-1,1,1-dioxo-7-[1-(2,2,2-trifluoro-ethoxyimino)-ethyl]-1,4,4a,5,5a,6,11,12a-octahydro-naphthacene-2-carboxylic acid amide (Compound AW)

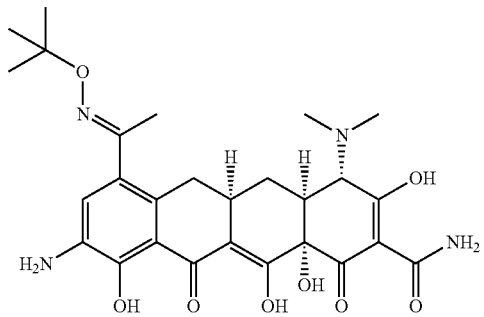 [SMILES: C/C(=N\OC(C)(C)C)c1cc(N)c(O)c2c1C[C@H]1C[C@H]3[C@H](N(C)C)C(O)=C(C(N)=O)C(=O)[C@@]3(O)C(O)=C1C2=O]

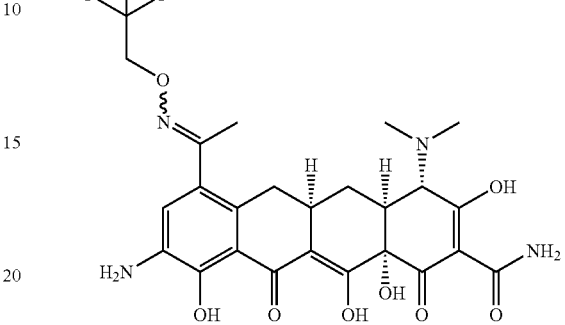

A mixture of 7-iodo-9-nitrosancycline (10 mmol), Pd(PPh$_3$)$_4$ (0.5 mmol), Pd(OAc)$_2$ (0.5 mmol), CuI (0.5 mmol) in acetonitrile (80 mL) was cooled with an ice-bath and purged with argon. While under argon atmosphere and at an ice bath temperature, triethylamine (50 mmol) and trimethylacetylene (15 mmol) were added. The ice-bath was removed and the reaction mixture was stirred for 1.75 hours. The acetonitrile was partially removed. To the crude intermediate at an ice-bath temperature a sulfuric acid solution (conc H$_2$SO$_4$:H$_2$O, 4/1, 50 mL) was slowly added and the solution was stirred for 10 minutes. The crude product was slowly poured on to 3 L of deionized water and filtered through celite pad. The filtrate was taken and the compound was purified using short DVB column to give 7-acetyl-9-nitrosancycline.

To a mixture of 7-acetyl-9-nitrosancycline (0.94 mmol) and Pd—C (5%, 53% water, 290 mg) in methanol (30 mL) was added a few drops of acetic acid. The reaction mixture was purged with H$_2$ and stirred under H$_2$ atmosphere at 20 psi for 1 hour. The reaction mixture was then filtered through celite, the filtrate was taken, solvent was evaporated and purified by prep-HPLC using C18 column (linear gradient 5-30% acetonitrile in water with 0.1% TFA) to give 7-acetyl-9-aminosancycline.

A solution of 7-acetyl-9-aminosancycline hydrochloride (0.79 mmol) and O-tert-butylhydroxylamine hydrochloride (4.74 mmol) in methanol (10 mL) was stirred overnight. The methanol was evaporated and the resulting compound purified by prep-HPLC using C18 column (linear gradient 15-35% acetonitrile in water with 0.1% TFA) to give a yellow solid: MS (Mz+1=543); $^1$H NMR (300 MHz, CD$_3$OD) δ 7.54. (s, 1H), 4.14 (s, 1H), 3.14-2.99 (9H), 2.52 (m, 1H), 2.20 (m, 1H), 2.16 (s, 3H), 1.32 (s, 9H). Compounds M and R were also prepared in a similar manner and compound BE may also be prepared in a similar manner.

A solution of 7-acetyl-9-amino-sancycline (1.5 mmol) and 2,2,2-trifluoroethylhydroxylamine hydrochloride (3 mmol) in methanol (20 mL) was stirred overnight. The methanol was evaporated and the crude product was purified by prep-HPLC using C18 column (linear gradient 10-35% acetonitrile in water with 0.1% TFA) to give a yellow solid: MS (Mz+1=569); NMR (300 MHz, CD$_3$OD) δ 7.48 (s, 1H), 4.63 (d, 1H, J=8.9 Hz), 4.57 (d, 1H, J=8.9 Hz), 4.12 (d, 1H, J=0.9 Hz), 3.10-2.96 (9H), 2.50 (m, 1H), 2.22 (s, 3H), 2.18 (m, 1H), 1.62 (m, 1H). Compounds M and R were also prepared in a similar manner and compound BE may also be prepared in a similar manner.

(4S,4aS,5aR,12aS)-4-Dimethylamino-7-(ethoxyamino-methyl)-3,10,12,12a-tetrahydroxy-1,11-dioxo-1,4,4a,5,5a,6,11,12a-octahydro-naphthacene-2-carboxylic acid amide (Compound AA)

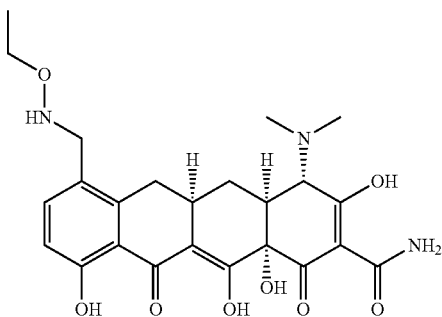 [SMILES: CCONCc1ccc(O)c2c1C[C@H]1C[C@H]3[C@H](N(C)C)C(O)=C(C(N)=O)C(=O)[C@@]3(O)C(O)=C1C2=O]

An amount of 7-formyl-sancycline (1.5 g, 3.39 mmol) was combined with methanol (30 mL) and O-(ethoxy)methylamine (1.5 g, 15.5 mmol) and was stirred at room temperature under a blanket of argon. The reaction was monitored by HPLC and LC/MS, which indicated that the reaction was complete in about 3 hours. The solvent was evaporated in vacuo and the resulting yellow solid was dried. A yellow solid (2.3 g) was isolated as an oxime. LC/MS: (m/z+1) 485.

The oxime (2.3 g, 4.72 mmol) was suspended in methanol saturated with HCl (45 mL) and cooled in an ice bath. An amount of NaCNBH₃ (585 mg, 9.44 mmol) was added in small batches followed by a few drops of methanol saturated with HCl via syringe. The reducing agent was added over the course of about two hours. The reaction was monitored by HPLC and LC/MS and was complete within 2 hours. The solvent was evaporated in vacuo and was purified in 5 batches on preparatory HPLC using C18 column (linear gradient 10-45% acetonitrile in 20 mM aqueous triethanolamine, pH 7.4).

The purified compound was dried in vacuo and redissolved in methanol (20 mL) saturated with HCl to exchange the salt. The compound was dried overnight over $P_2O_5$ to yield the product (0.21 mg, 13%) as a yellow powder. ESI-MS: (MH+)=488. ¹H NMR (300 MHz, CD₃OD) δ 7.63 (1H, d, J=9 Hz), 6.93 (1H, d, J=9 Hz), 4.53 (s, 1H), 4.17 (m, 3H), 3.25 (m, 1H), 3.07 (m, 8H), 2.44 (m, 1H), 2.31 (m, 1H), 1.62 (m, 1H), 1.29 (3H, t, J=7 Hz). Compounds AM, AB, AE, AR, AS, AT, AU, AY, AF and AX were also prepared in a similar manner and compounds AG, BA, BB, BC and BD may be prepared in a similar manner.

(4S,4aS,5aR,12aS)-4-Dimethylamino-3,10,12,12a-tetrahydroxy-7-(isopropoxyamino-methyl)-1,11-dioxo-1,4,4a,5,5a,6,11,12a-octahydro-naphthacene-2-carboxylic acid amide (Compound AN)

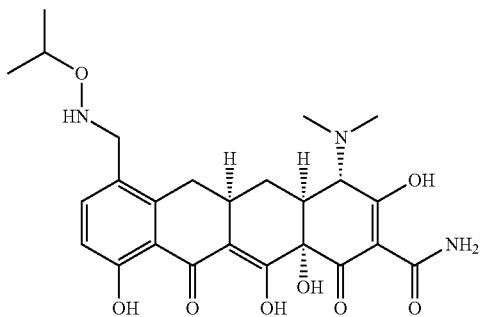 [SMILES: CC(C)ONCc1ccc(O)c2c1C[C@H]1C[C@H]3[C@H](N(C)C)C(O)=C(C(N)=O)C(=O)[C@@]3(O)C(O)=C1C2=O]

A solution of 7-formylsancycline (1.8 mmol) and O-isopropylhydroxylamine hydrochloride (9 mmol) in methanol (25 mL) was stirred overnight. The solvent was reduced and the crude product was used for the next reaction without further purification. A solution of 7-(isopropoxyimino-methyl)-sancycline (2 mmol) in methanol saturated with HCl was cooled in an ice-bath and NaCNBH₃ was added portion-wise while stirring at the same temperature. The solvent was reduced and the crude product was purified by prep-HPLC using C18 column (linear gradient 15-30% acetonitrile in 20 mM aqueous triethanolamine, pH 7.4) to give a yellow solid: MS (Mz+1=502); ¹H NMR (300 MHz, CD₃OD) δ 7.63 (d, 1H, J=8.7 Hz), 6.92 (d, 1H, J=8.7 Hz), 4.44 (m, 1H), 4.14 (d, 1H, J=1.2 Hz), 3.27-2.97 (9H), 2.43 (t, 1H, J=14.4), 2.27 (m, 1H), 1.29 (m, 6H). Compounds AM, AB, AE, AR, AS, AT, AU, AY, AF and AX were prepared in a similar manner and compounds AG, BA, BB, BC and BD may be prepared in a similar manner.

(4S,4aS,5aR,12aS)-4-Dimethylamino-7-[(2-fluoro-ethoxyamino)-methyl]-3,10,12,12a-tetrahydroy-1,11-dioxo-1,4,4a,5,5a,6,11,12a-octahydro-naphthacene-2-carboxylic acid amide (Compound AO)

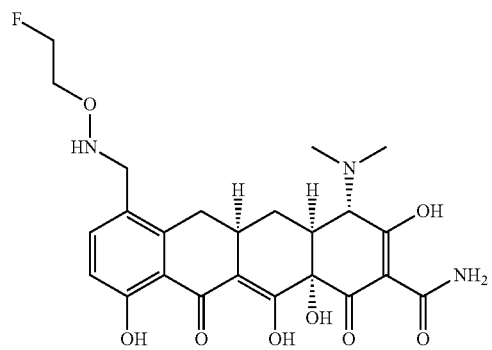 [SMILES: CN(C)[C@@H]1C(O)=C(C(N)=O)C(=O)[C@@]2(O)C(O)=C3C(=O)c4c(O)ccc(CNOCCF)c4C[C@H]3C[C@@H]12]

A solution of 7-formylsancyline (4 mmol) and 2-fluoro-ethylhydroxylamine hydrochloride (10 mmol) in methanol (50 mL) was stirred overnight, after which LC-MS showed completion of the reaction. The methanol was reduced and the crude product was used for the next reaction without further purification. To a cooled solution of 7-(2'-fluoro-ethoxyimino-methyl)-sancycline (2 mmol) in methanol saturated with HCl was added portion-wise NaCNBH₃ (8 mmol) over 8 hours while stirring at the same temperature. The solvent was reduced and the crude product was purified by prep-HPLC using C18 column (linear gradient 10-40% acetonitrile in 20 mM aqueous triethanolamine, pH 7.4) to give a yellow solid: MS (Mz+1=506); ¹H NMR (300 MHz, CD₃OD) δ 7.65 (d, 1H, J=8.8 Hz), 6.93 (d, 1H, J=8.8 Hz), 4.75 (m, 1H), 4.61-4.55 (3H), 4.46 (m, 1H), 4.36 (m, 1H), 4.16 (d, 1H, J=1.2 Hz), 3.26-2.97 (9H), 2.45 (t, 1H, J=14.4), 2.31 (m, 1H), 1.63 (m, 1H). Compounds AM, AB, AE, AR, AS, AT, AU, AY, AF and AX were prepared in a similar manner and compounds AG, BA, BB, BC and BD may be prepared in a similar manner.

4S,4aS,5aR,12aS)-4-Dimethylamino-3,10,12,12a-tetrahydroxy-7-(3-imino-isoxazolidin-2-ylmethyl)-1,11-dioxo-1,4,4a,5,5a,6,11,12a-octahydro-naphthacene-2-carboxylic acid amide (Compound AZ)

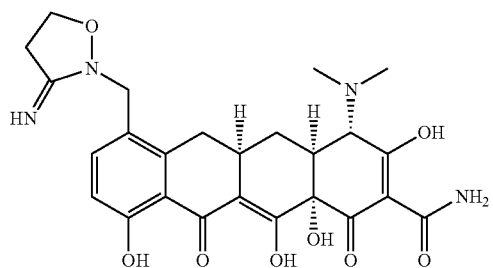 [SMILES: CN(C)[C@@H]1C(O)=C(C(N)=O)C(=O)[C@@]2(O)C(O)=C3C(=O)c4c(O)ccc(CN5OCCC5=N)c4C[C@H]3C[C@@H]12]

A solution of 7-formylsancycline (2 mmol) and 3-aminooxy-propiononitrile (4 mmol) in methanol (30 mL) was stirred overnight. The solvent was reduced and the crude product was used for the next reaction without further purification. A solution of 7-(2'-cyanoethoxyimmuno-methyl)-sancycline in methanol with HCl was cooled with an ice-bath. An amount of NaCNBH₃ was added portionwise and stirred for 1.5 hours. The solvent was evaporated and purified by prep-HPLC using C-18 column (linear gradient 10-40% acetonitrile in 20 mM aqueous triethanolamine, pH 7.4) to give a yellow solid: MS (Mz+1=513); $^1$H NMR (300 MHz, CD₃OD) δ 7.47 (d, 1H, J=8.8 Hz), 6.86 (d, 1H, J=8.8 Hz), 5.11 (d, 1H, J=15.9 Hz), 4.96 (d, 1H, J=15.9 Hz), 4.41 (m, 2H), 4.11 (s, 1H), 3.50 (t, 2H, J=8.4 Hz), 3.20-2.94 (9H), 2.38 (t, 1H, J=15.3 Hz), 2.28 (m, 1H), 1.60 (m, 1H). Compounds AM, AB, AE, AR, AS, AT, AU, AY, AF and AX were prepared in a similar manner and compounds AG, BA, BB, BC and BD may be prepared in a similar manner.

(4S,4aS,5aR,12aS)-4-Dimethylamino-3,12,12a-trihydroxy-1,11-dioxo-7-pyrazin-2-yl-1,4,4a,5,5a,6,11,12a-octahydro-naphthacene-2-carboxylic acid amide (Compound W)

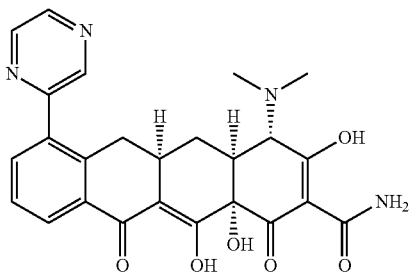 [SMILES: CN(C)[C@@H]1C(O)=C(C(N)=O)C(=O)[C@@]2(O)C(O)=C3C(=O)c4cccc(-c5cnccn5)c4C[C@H]3C[C@@H]12]

An amount of 7-iodo-sancycline (1 g, 1.53 mmol) was combined with CuI (0.029 g, 0.153 mmol), Pd₂(dba)₃ (0.140 g, 0.153 mmol), tri-2-furylphosphine (0.284 g, 0.153 mmol), 2-tributylstannylpyrazine (0.677 g, 0.184 mmol), and DMF (6 mL) in a 20 mL glass microwave vial. The reaction mixture was placed in the microwave for 10 minutes at 100° C. on high absorbance. The solvent was evaporated in vacuo. The free-base of the this compound was made by pouring 8 g of product into 1.8 L water (0.1% TFA). To the resulting heterogeneous mixture, celite was added and the material was filtered through a celite plug. The water filtrate was loaded onto a prepared DVB column, and washed with water (0.1% TFA) and 0.25 M NaOAc until a basic pH of the eluent was obtained. The DVB column was then washed with distilled water until a neutral pH was obtained and the compound was then eluted as the free-base with CH₃CN.

An amount of 7-pyrazine-sancycline-free base (1 g, 0.209 mmol) was combined with dry THF (15 mL) in a 100 mL 2 neck round bottom flask. The reaction solution was cooled in an ice bath under a blanket of argon and potassium t-butoxide (1.17 g, 1.04 mmol) was added in one portion. The resulting heterogeneous mixture was stirred in an ice bath for 45 minutes. To this was added N-phenylbis-(trifluoromethanesulfonamide) (1.49 g, 4.18 mmol) in one portion. The resulting homogeneous solution was stirred in an ice bath for 45 minutes, then warmed to room temperature and reaction solution was stirred for another 1 hour. The reaction mixture was poured into 200 mL 0.5 M HCl, celite was added, and the mixture was filtered through a celite plug. The water filtrate was loaded onto a prepared DVB column, washed with 0.5 M HCl, water, then eluted product with CH₃CN (0.1% TFA). The product was evaporated to dryness and purified on a prep-HPLC using C-18 column. Clean fractions were evaporated to dryness.

An amount 7-pyrazine-10-triflate-sancycline (0.220 g, 0.352 mmol) was combined with ammonium formate (0.112 g, 1.77 mmol), lithium chloride (0.074 g, 1.77 mmol), Pd₂(dppf)₂Cl₂ (0.052 g, 0.071 mmol), DMA (1.5 mL), and water (1.5 mL) in a glass microwave vial. The reaction mixture was purged with argon and placed in microwave for 10 minutes at 100° C. on high absorbance. The reaction solution was poured into 100 mL water (0.1% TFA), and filtered through celite. The resulting yellow eluent was loaded onto a prepared 2 g DVB cartridge and eluted with CH₃CN (0.1% TFA). The solvent was evaporated and purified on a prep-HPLC using C18 column (linear gradient 5-45% acetonitrile in water with 0.1% TFA). The purified compound was dried in vacuo and re-dissolved in methanol (20 mL) saturated with HCl to exchange the salt. The compound was dried overnight over P₂O₅ to yield the product (0.035 g, 16%) as a yellow powder. ESI-MS: (MH+)=477. $^1$H NMR (300 MHz, CD₃OD) δ 8.77 (m, 1H), 8.71 (m, 1H), 8.63 (m, 1H), 8.14 (m, 11-1), 7.71 (m, 1H), 7.57 (m, 1H), 3.99 (m, 1H), 2.97 (m, 9H), 2.63 (m, 1H), 2.04 (m, 1H), 1.62 (m, 1H) Compounds D, E, F, G and S were also prepared in a similar manner.

(4S,4aS,5aR,12aS)-4-Dimethylamino-3,10,12,12a-tetrahydroxy-1,11-dioxo-7-(1H-pyrrol-2-yl)-1,4,4a,5,5a,6,11,12a-octahydro-naphthacene-2-carboxylic acid amide (Compound T)

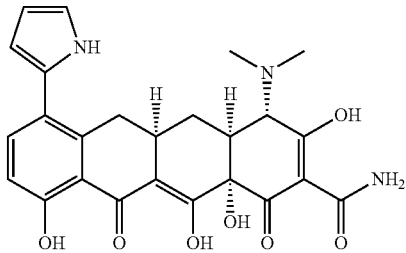 [SMILES: CN(C)[C@@H]1C(O)=C(C(N)=O)C(=O)[C@@]2(O)C(O)=C3C(=O)c4c(O)ccc(-c5ccc[nH]5)c4C[C@H]3C[C@@H]12]

An amount of 7-iodo-sancycline (1 g, 1.53 mmol) was combined with Pd(OAc)₂ (0.034 g, 0.153 mmol), methanol (1 mL), and DMF (2 mL) in a glass microwave vial. The reaction mixture was purged with argon and an amount of Na₂CO₃ (0.482 g, 4.59 mmol) dissolved in water (1 mL) was added by syringe into reaction vessel resulting in a heterogeneous mixture. An amount of 1-N-Boc-pyrrole-2-boronic acid (0.645 g, 3.06 mmol) was dissolved in DMF (1 mL) and was added by syringe into the reaction vessel. The resulting mixture was microwaved for 10 minutes at 100° C. On completion of the reaction, the mixture was filtered through celite and the solvent was reduced in vacuo. The crude reaction mixture was then triturated with 500 mL diethyl ether to yield a yellow precipitate. The precipitate was filtered, rinsed with fresh diethyl ether, and dried under vacuum to yield 700 mg of yellow solid. This yellow material was then added to TFA (10 mL) and stirred at room temperature for 5 minutes. The solvent was reduced and the crude product was purified by prep-HPLC using C18 column (linear gradient 15-50% acetonitrile in water with 0.1% TFA). The purified compound was dried in vacuo and redissolved in methanol (20 mL) saturated with HCl to exchange the salt. The compound was dried overnight over $P_2O_5$ to yield the product (0.020 g, 3%) as a yellow powder. ESI-MS: (MH+)=480. $^1$H NMR (300 MHz, $CD_3OD$) δ 7.53 (1H, d, J=9 Hz), 6.87 (1H, d, J=9 Hz), 6.80 (m, 1H), 6.16 (m, 1H), 6.08 (m, 1H), 4.06 (s, 1H), 3.18 (m, 1H), 2.98 (m, 9H), 2.49 (m, 1H), 2.09 (m, 1H), 1.61 (m, 1H). Compounds J, K and L were also prepared in a similar manner.

(4R,4aS,5aR,12aS)-4-Dimethylamino-7-(3-dimethylamino-1-ethoxyimino-propyl)-3,10,12,12a-tetrahydroxy-1,11-dioxo-1,4,4a,5,5a,6,11,12a-octahydro-naphthacene-2-carboxylic acid amide (Compound I)

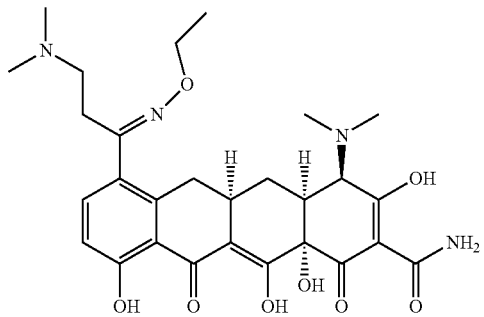 [SMILES: CCO/N=C(\CCN(C)C)c1ccc(O)c2c1C[C@H]1C[C@H]3[C@@H](N(C)C)C(O)=C(C(N)=O)C(=O)[C@@]3(O)C(O)=C1C2=O]

A mixture of 7-iodosancycline (5 mmol), (O-tolyl)$_3$P (1 mmol), Pd(PPh$_3$)$_4$ (1 mmol), Pd(OAc)$_2$ (1 mmol), CuI (1 mmol)) and triethylamine in acetonitrile (45 mL) was purged with argon. An amount of 1-N,N-dimethylamino-2-propyne was added and the reaction mixture was slowly (~40 minutes) warmed up to 50° C. The reaction mixture was then poured into 1 L of 0.1% TFA in water and filtered through a celite pad. The filtrate was taken and water was removed using short column of DVB. The crude product was used for the next reaction without further purification.

An amount of 7-(3'-dimethylamino)-prop-1-ynyl-sancycline (the crude product from the above reaction) was dissolved in a cooled $H_2SO_4$ solution (conc $H_2SO_4$:$H_2O$, 4/1, 35 mL) at an ice-bath temperature. The reaction mixture was stirred for 5 minutes and was poured into acidic water (0.1% TFA, 1 L). The resulting solution was then filtered through celite pad and water was removed using short column of DVB. The compound was purified by prep-HPLC using C18 column (linear gradient 5-30% acetonitrile in water with 0.1% TFA).

A solution of 7-(3'-dimethylamino-propionyl)-sancycline (5.12 mmol) and O-ethoxylamine hydrochloride (41 mmol) in N,N-dimethylacetamide was stirred at 80° C. under microwave conditions for 70 minutes. The product was purified by prep-HPLC using C18 column (linear gradient 10-40% acetonitrile in water with 0.1% TFA) to give a yellow solid: MS (Mz+1=557); NMR (300 MHz, CD$_3$OD) δ 7.39 (m, 1H), 6.91 (m, 1H), 4.86 (11-1, d, J=3.9 Hz), 4.26-4.08 (m, 2H), 3.5 (m, 1H), 3.30-2.87 (18H), 2.50 (m, 1H), 2.20 (m, 1H), 1.56 (m, 1H), 1.36-1.19 (m, 3H). Compound 0 was also prepared in a similar manner.

(4S,4aS,5aR,12aS)-4-Dimethylamino-3,10,12,12a-tetrahydroxy-1,11-dioxo-7-(pyrrol-1-yliminomethyl)-1,4,4a,5,5a,6,11,12a-octahydro-naphthacene-2-carboxylic acid amide (Compound AC)

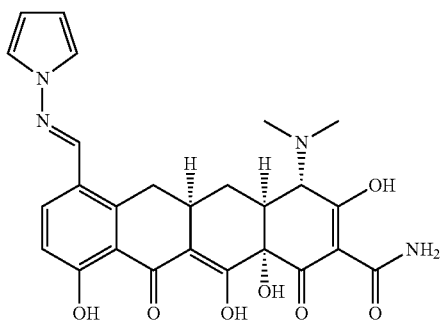 [SMILES: CN(C)[C@@H]1C(O)=C(C(N)=O)C(=O)[C@@]2(O)C(O)=C3C(=O)c4c(O)ccc(/C=N/n5cccc5)c4C[C@H]3C[C@@H]12]

An amount of 7-formyl sancycline (0.4 g, 0.905 mmol) was combined with 1-aminopyrrole (0.223 g, 2.71 mmol) and DMA (8 mL) in a glass vial. The reaction mixture was stirred at room temperature under a blanket of argon for 30 minutes. The crude reaction mixture was poured into water (0.1% TFA) (100 mL) and loaded onto a prepared 5 g DVB cartridge, which was then washed with water and eluted with CH$_3$CN (0.1% TFA). After evaporating the volatiles, the resulting compound was purified by prep-HPLC using C18 column (linear gradient 10-70% acetonitrile in 20 mM aqueous triethanolamine, pH 7.4). The purified compound was dried in vacuo and redissolved in methanol (20 mL) saturated with HCl to exchange the salt. The compound was dried overnight over P$_2$O$_5$ to yield the product (0.035 g, 8%) as a yellow powder. ESI-MS: (MH+)=507. $^1$H NMR (300 MHz, CD$_3$OD) δ 8.78 (s, 1H), 8.12 (1H, d, J=9 Hz), 7.23 (2H, t, J=3 Hz), 6.93 (1H, d, J=9 Hz), 6.17 (2H, t, J=3 Hz), 4.08 (s, 1H), 3.54 (m, 1H), 2.97 (m, 9H), 2.47 (m, 1H), 2.24 (m, 1H), 1.65 (m, 1H). Compound X was also prepared in a similar manner.

(4S,4aS,5aR,12aS)-7-(N,N''-Diethyl-hydrazinomethyl)-4-dimethylamino-3,10,12,12a-tetrahydroxy-1,11-dioxo-1,4,4a,5,5a,6,11,12a-octahydro-naphthacene-2-carboxylic acid amide (Compound Z)

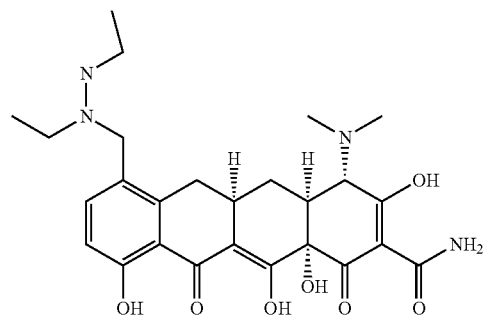 [SMILES: CCNN(CC)Cc1ccc(O)c2c1C[C@H]1C[C@H]3[C@H](N(C)C)C(O)=C(C(N)=O)C(=O)[C@@]3(O)C(O)=C1C2=O]

An amount of 7-formyl sancycline (0.5 g, 1.13 mmol) was combined with 1,2-diethylhydrazine (0.546 g, 3.39 mmol), triethylamine (0.472 g, 3.39 mmol), and DMA (10 mL) in a glass vial. The resulting heterogeneous mixture was stirred at room temperature under a blanket of argon for 45 minutes. An amount of NaCNBH₃ (0.084 g, 1.36 mmol) was added to the reaction mixture and stirred overnight at room temperature. The reaction mixture was poured into water (0.1% TFA), loaded onto a prepared 5 g DVB cartridge, and eluted with CH₃CN (0.1% TFA). After evaporating volatiles, the crude product was purified on a prep-HPLC using C18 column (linear gradient 5-60% acetonitrile in 20 mM aqueous triethanolamine, pH 7.4). The purified compound was dried in vacuo and redissolved in methanol (20 mL) saturated with HCl to exchange the salt. The compound was dried overnight over $P_2O_5$ to yield the product (0.030 g, 6%) as a yellow powder. ESI-MS: (MH+)=515. ¹H NMR (300 MHz, CD₃OD) δ 7.53 (1H, d, J=9 Hz), 6.87 (1H, d, J=9 Hz), 4.18 (m, 1H), 4.06 (s, 2H), 3.19 (m, 1H), 3.00 (m, 10H), 2.40 (m, 1H), 2.20 (m, 1H), 1.64 (m, 1H), 1.24 (3H, t, J=9 Hz), 1.13 (m, 3H).

Allyl-((6a5,10S,10aS,11aR)-8-carbamoyl-10-dimethylamino-4,6,6a,9-tetrahydroxy-5,7-dioxo-5,6a,7,10,10a,11,11a,12-octahydro-naphthacen-1-ylmethyl)-carbamic acid methyl ester (Compound F)

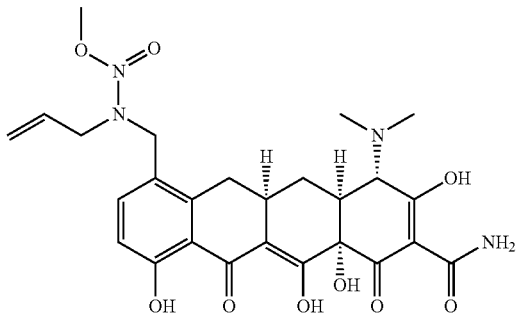

A solution of 7-formylsancycline (1.5 mmol) and allylamine (4.5 mmol) in 1,2-dichloroethane (50 mL) was stirred for 30 minutes. Sodium triacetoxyborohydride was added and stirred for an additional 3 hours. The solvent and excess reagent were evaporated and the crude material was purified by prep-HPLC to give 7-allylaminomethyl-sancycline as a yellow solid: MS (Mz+1=484).

To a solution of 7-allylaminomethyl-sancycline (0.78 mmol) in N,N-dimethylacetamide (7 mL) was added methylchloroformate (1.6 mmol) dropwise and the reaction mixture was stirred for 1 hour. An additional amount of methylchloroformate (1.6 mmol) was added and stirred for additional 3 hours. The resulting product was purified by prep-HPLC using C18 column (linear gradient 15-30% acetonitrile in water with 0.2% formic acid) to give a yellow solid: MS (Mz+1=542); ¹H NMR (300 MHz, CD₃OD) δ 7.34 (1H, d, J=8.5 Hz), 6.82 (1H, d, J=8.5 Hz), 5.71 (m, 1H), 5.06 (m, 2H), 4.47 (m, 2H), 4.08 (1H, d, J=0.9 Hz), 3.84-3.65 (m, 2H), 3.71 (s, 3H), 3.21-2.92 (9H), 2.30-1.94 (2H), 1.59 (m, 1H).

(4S,4aS,5aR,12aS)-4,7-Bis-dimethylamino-3,10,12,12a-tetrahydroxy-9-(methoxyimino-methyl)-1,11-dioxo-1,4,4a,5,5a,6,11,12a-octahydro-naphthacene-2-carboxylic acid amide (Compound V)

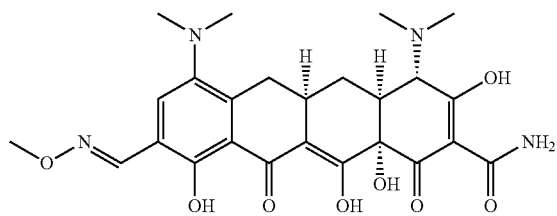 [SMILES: CO/N=C/c1cc(N(C)C)c2c(c1O)C(=O)C1=C(O)[C@]3(O)C(=O)C(C(N)=O)=C(O)[C@@H](N(C)C)[C@@H]3C[C@@H]1C2]

A solution of 9-formylminocycline (1.19 mmol) and O-methylhydroxylamine hydrochloride (5.96 mmol) in methanol (15 mL) was stirred for 1.5 hours. The solvent was evaporated and purified by prep-HPLC using C18 column (linear gradient 10-50% acetonitrile in 20 mM aqueous triethanolamine, pH 7.4) to give a yellow solid: MS (Mz+1=515); ¹H NMR (300 MHz, CD₃OD) δ 8.42 (s, 1H), 8.09 (s, 1H), 4.13 (1H, d, J=1.2 Hz), 3.99 (s, 31-1), 3.35 (m, 1H), 3.09-2.98 (14H), 2.43 (m, 1H), 2.24 (m, 1H), 1.69 (m, 1H). Compounds AK and AH may also be prepared in a similar manner.

(4S,4aS,5aR,12aS)-4-Dimethylamino-3,10,12,12a-tetrahydroxy-7-(2-methylamino-3,4-dioxo-cyclobut-1-enyl)-1,11-dioxo-1,4,4a,5,5a,6,11,12a-octahydro-naphthacene-2-carboxylic acid amide (Compound AD)

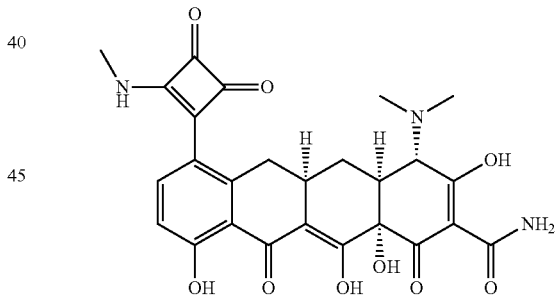

A mixture of 7-iodosancycline (2 mmol), 3-isopropoxy-4-tributylstannanyl-cyclobut-3-ene-1,2-dione (4.4 mmol), tetrakis(triphenylphosphine)palladium (0.4 mmol) and CuI (0.4 mmol) in N,N-dimethylacetamide was microwave irradiated for 50 minutes at 80° C. The resulting compound was purified using a DVB column to give 7-(2'-isopropoxy-3',4'-dioxo-cyclobut-1'-enyl)-sancycline as a yellow solid: MS (Mz+1=553).

To a solution of 7-(2'-isopropoxy-3',4'-dioxo-cyclobut-1'-enyl)-sancycline (0.9 mmol) in methanol (20 mL) was added 1 mL of 33% methylamine in absolute ethanol and the reaction mixture was stirred for 40 minutes. The resulting product was purified by prep-HPLC using C18 (linear gradient 10-40% acetonitrile in 20 mM aqueous triethanolamine, pH 7.4) column to give a yellow solid: MS (Mz+1=524); $^1$H NMR (300 MHz, CD$_3$OD) δ 7.46 (1H, d, J=8.7 Hz), 6.88 (1H, d, J=8.7 Hz), 4.01 (s, 1H), 3.27 (s, 3H), 3.07-2.82 (9H), 2.45 (m, 1H), 2.10 (m, 1H), 1.52 (m, 1H). Compounds AI and AJ may also be prepared in a similar manner.

(4S,4aS,5aR,12aS)-4-Dimethylamino-7-{[(2-ethoxy-imino-propyl)-methyl-amino]-methyl}-3,10,12,12a-tetrahydroxy-1,11-dioxo-1,4,4a,5,5a,6,11,12a-octa-hydro-naphthacene-2-carboxylic acid amide (Compound AL)

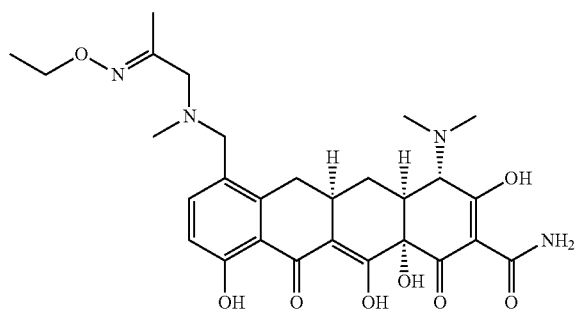 [SMILES: CCO/N=C(\C)CN(C)Cc1ccc(O)c2c1C[C@H]1C[C@H]3[C@H](N(C)C)C(O)=C(C(N)=O)C(=O)[C@@]3(O)C(O)=C1C2=O]

A solution of 7-formylsancycline (2 mmol) and methyl-(2-methyl-[1,3]dioxolan-2-ylmethyl)-amine (6 mmol) in N,N-dimethylformamide (30 mL) was stirred for 40 minutes. Sodium triacetoxyborohydride (6 mmol) was added and the reaction was stirred for 6 hours. The solvent was evaporated and the crude material was dissolved in a mixture of tetrahydrofuran (10 mL), acetic acid (10 mL) and 6M HCl (10 mL). This solution was stirred at 60° C. for 6 hours. Upon completion, the solvent and excess reagents were evaporated and the crude material was purified by prep-HPLC to give 7-{[(methyl-2'-oxo-propyl)-methyl-amino]-methyl}-sancycline as a yellow solid: MS (Mz+1=514).

A solution of 7-{[(methyl-2'-oxo-propyl)-methyl-amino]-methyl}-sancycline (0.63 mmol) and O-ethylhydroxyamine hydrochloride (3.15 mmol) in methanol (15 mL) was stirred for 8 hours. The solvent was evaporated and purified by prep-HPLC using C18 column (linear gradient 20-50% acetonitrile in 20 mM aqueous triethanolamine, pH 7.4) to give a yellow solid: MS (Mz+1=599); $^1$H NMR (300 MHz, CD$_3$OD) δ 7.69 (1H, d, J=8.7 Hz), 6.99 (1H, d, J=8.7 Hz), 4.65 (m, 1H), 4.35 (m, 1H), 4.24 (2H, q, J=7.1 Hz), 4.15 (s, 1H), 4.07 (brs, 2H), 3.24-2.85 (12H), 2.50 (m, 1H), 2.30 (m, 1H), 1.95 (s, 3H), 1.52 (m, 1H), 1.31 (3H, t, J=7.1 Hz).

(4S,4aS,5aR,12aS)-4-Dimethylamino-9-[(methoxy-methyl-amino)-methyl-3,10,12,12a-tetrahydroxy-1,11-dioxo-1,4,4a,5,5a,6,11,12a-octahydro-naphthacene-2-carboxylic acid amide (Compound AP)

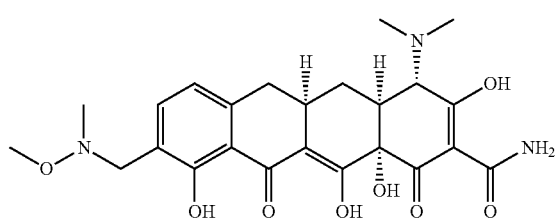 [SMILES: CON(C)Cc1ccc2c(c1O)C(=O)C1=C(O)[C@]3(O)C(=O)C(C(N)=O)=C(O)[C@@H](N(C)C)[C@@H]3C[C@@H]1C2]

An amount of 7-bromo-9-formyl-sancycline (1.92 mmol) was combined with N,O-dimethyl-hydroxylamine HCl salt (3.84 mmol) and DMA (8 mL) and stirred under an argon atmosphere at room temperature for 1.5 hours. An amount of sodium cyanoborohydride (2.3 mmol) was added and the reaction was monitored by LC/MS. The reaction mixture was triturated in diethyl ether (300 mL), and filtered to give 1.3 g of 7-bromo-9-methoxyaminomethyl sancycline.

An amount of 7-bromo-9-methoxyaminomethyl sancycline (0.88 mmol) was combined with ammonium formate (8.83 mmol), Pd(dppf)$_2$CH$_2$Cl$_2$ (0.0883 mmol), InCl$_3$ (0.442 mmol), and NMP (7 mL) in a microwave vial and placed in the microwave on high absorbance for 5 minutes at 100° C. The reaction mixture was poured into water (400 mL with 0.1% TFA) and was filtered through celite. The crude product was purified by prep-HPLC using a C-18 column (linear gradient 10-40% acetonitrile in water with 0.1% TFA). ESI-MS: (MH+)=488. $^1$H NMR (300 MHz, CD$_3$OD) δ 7.64 (1H, d, J=9 Hz), 6.90 (1H, d, J=6 Hz), 4.67 (m, 21-1), 4.11 (s, 1H), 3.98 (m, 3H), 3.17 (m, 411), 2.97 (m, 9H), 2.61 (m, 1H), 2.23 (m, 1H), 1.61 (m, 1H).

Example 2

Anti-Bacterial Activity

In this example, the gram (+) and gram (−) antibacterial activities of the tetracycline compounds used in the methods of the invention were assessed.

Gram (−) and gram (+) antibacterial minimum inhibitory concentration (MIC) values (μg/mL) were obtained using CLSI methodology for anti-bacterial susceptibility testing. On each day of testing, serial dilutions of compounds were prepared in microdilution plates using a Tecan robotic workstation. Mueller Hinton broth cultures of representative sensitive and resistant gram negative strains were grown or adjusted to match the turbidity of a 0.5 McFarland standard. 1:200 dilutions were made in an appropriate broth (cation supplemented Mueller Hinton broth) to allow a final inoculum of 1×10$^5$ cfu. Plates were incubated at 35° C. in ambient air for 18-24 hours, were read spectrophotometrically and checked manually for evidence of bacterial growth. The lowest dilution of compound that inhibited growth was recorded as the MIC. Lysed horse blood was used to supplement broth for testing *S. pneumoniae*. The MIC's for each compound were assessed against *S. aureus, S. pneumoniae, P. acnes, E. coli* and *B. theta*. The results are shown in Table 3. Good antibacterial activity (e.g., less than about 4 μg/mL) is indicated by "*," modest antibacterial activity (between about 4 and 8 μg/mL) is indicated by "," or weak antibacterial activity (greater than about 8 μg/mL) is indicated by "*." The symbol "−" indicates that no data was obtained.

TABLE 3

| Compound Code | S. aureus RN450 | S. pneumoniae 157E - Strep | P. acnes ATCC 6919 | P. acnes ATCC 11827 | E. coli ATCC 25922 | E. coli MG. 1655 | B. thetaiotaomicron ATCC 29741 |
|---|---|---|---|---|---|---|---|
| A | *** | *** | *** | *** | *** | ** | * |
| B | *** | *** | *** | *** | * | * | ** |
| C | *** | *** | *** | *** | * | * | * |
| D | *** | *** | ** | ** | * | * | * |
| E | *** | *** | *** | *** | ** | * | * |
| F | *** | *** | *** | *** | * | * | ** |
| G | *** | *** | ** | ** | ** | * | * |
| H | *** | *** | ** | ** | * | * | * |
| I | *** | *** | *** | *** | *** | *** | ** |
| J | *** | *** | *** | *** | *** | *** | *** |
| K | *** | *** | *** | *** | *** | *** | *** |
| L | *** | *** | *** | *** | *** | *** | *** |
| M | *** | *** | *** | *** | *** | ** | ** |
| N | *** | *** | *** | *** | *** | ** | *** |
| O | *** | *** | *** | *** | *** | *** | *** |
| P | *** | *** | *** | *** | ** | ** | ** |
| Q | *** | *** | *** | *** | ** | ** | ** |
| R | *** | *** | *** | *** | * | * | ** |
| S | *** | *** | ** | ** | * | * | * |
| T | *** | *** | *** | *** | *** | *** | ** |
| U | *** | *** | *** | *** | *** | ** | ** |
| V | *** | *** | *** | *** | * | * | ** |
| W | *** | *** | *** | *** | * | * | * |
| X | *** | *** | *** | *** | *** | *** | *** |
| Y | *** | ** | *** | *** | * | * | * |
| Z | *** | *** | *** | *** | ** | ** | * |
| AA | *** | *** | *** | *** | ** | ** | ** |
| AB | *** | *** | *** | *** | ** | * | ** |
| AC | *** | *** | *** | *** | ** | * | ** |
| AD | *** | *** | *** | *** | ** | ** | * |
| AE | *** | *** | *** | *** | ** | * | ** |
| AF | *** | *** | *** | *** | ** | ** | *** |
| AL | *** | *** | *** | *** | ** | ** | ** |
| AM | ** | ** | *** | *** | * | * | ** |
| AN | *** | *** | *** | *** | ** | * | ** |
| AO | *** | *** | *** | *** | *** | * | ** |
| AP | ** | ** | ** | ** | * | * | ** |
| AQ | *** | *** | *** | ** | * | * | ** |
| AR | *** | *** | *** | *** | ** | ** | *** |
| AS | *** | ** | *** | *** | * | * | ** |
| AT | *** | *** | *** | *** | ** | * | *** |
| AU | *** | ** | *** | *** | * | * | ** |
| AV | *** | *** | *** | *** | ** | * | ** |
| AW | *** | *** | *** | *** | ** | ** | ** |
| AX | *** | *** | *** | *** | ** | ** | *** |
| AY | *** | ** | *** | *** | * | * | ** |
| AZ | *** | *** | — | — | * | * | — |
| Doxycycline | *** | *** | *** | *** | *** | *** | ** |
| Minocycline | *** | *** | *** | *** | *** | *** | ** |

Example 3

Toxicity Profile

In this example, the cytotoxicity of the tetracycline compounds used in the methods of the invention were assessed.

Mammalian cell cytotoxicity was assessed to evaluate potential in vivo risks associated with the tetracycline compounds of the invention. A soluble, non-toxic redox dye ("Resazurin"; Alamar Blue) was used to assess a tetracycline compound's effect on cellular metabolism. At the onset of the experiment, cultures of mammalian COS-1 or CHO cells were washed, trypsinized, and harvested. Cell suspensions were prepared, seeded into 96-well black-walled microtiter plates, and incubated overnight at 37° C., in 5% $CO_2$ and approximately 95% humidity. On the next day, serial dilutions of test drug were prepared under sterile conditions and transferred to cell plates. Plates were then incubated under the above conditions for 24 hours. Following the incubation period, the media/drug was aspirated, and 50 μL of resazurin was added. Plates were then incubated under the above conditions for 2 hours and then in the dark at room temperature for an additional 30 minutes. Fluorescence measurements were taken (excitation 535 nm, emission 590 nm) and toxic effects in treated versus control cells were compared based on the degree of fluorescence in each well. The results are shown in Table 4. Minocycline and doxycycline toxicity scores are shown for comparison. Compounds which showed some cytotoxicity (e.g., less than about 35 μg/mL) to are indicated by "*," compounds which showed moderate cytotoxicity are indicated by "" (e.g., between about 35 and 75 μg/mL) and compounds that showed minimal cytotoxicity are indicated by "*" (e.g., greater than about 75 μg/mL).

TABLE 4

| Compound | COS-1 Cytotoxicity $IC_{50}$ (μg/mL) | CHO Cytotoxicity $IC_{50}$ (μg/mL) |
|---|---|---|
| Minocycline | * | * |
| Doxycycline | * | * |

TABLE 4-continued

| Compound | COS-1 Cytotoxicity IC$_{50}$ (µg/mL) | CHO Cytotoxicity IC$_{50}$ (µg/mL) |
|---|---|---|
| A | *** | *** |
| B | *** | *** |
| C | * | * |
| D | * | * |
| E | * | * |
| F | *** | *** |
| G | * | * |
| H | * | * |
| I | * | * |
| J | * | * |
| K | * | * |
| L | *** | *** |
| M | * | * |
| N | * | * |
| O | ** | *** |
| P | * | * |
| Q | *** | *** |
| R | * | * |
| S | * | * |
| T | *** | *** |
| U | * | ** |
| V | *** | *** |
| W | * | * |
| X | *** | *** |
| Y | * | * |
| Z | * | * |
| AA | * | * |
| AB | *** | *** |
| AC | *** | *** |
| AD | * | * |
| AE | * | *** |
| AF | ** | ** |
| AL | *** | *** |
| AM | * | * |
| AN | *** | *** |
| AO | * | * |
| AP | ** | ** |
| AQ | *** | *** |
| AR | *** | ** |
| AS | * | * |
| AT | *** | *** |
| AU | * | * |
| AV | ** | ** |
| AX | *** | *** |

Example 4

Phototoxic Potential

In this example, the phototoxic potential of the tetracycline compounds used in the methods of the invention was assessed. In particular, 3T3 fibroblast cells were harvested and plated at a concentration of 1×10$^5$ cells/mL and the plates were incubated overnight at 37° C., in 5% CO$_2$ and approximately 95% humidity. On the following day the medium was removed from the plates and replaced with Hanks' Balanced Salt Solution (HBSS). Drug dilutions were made in HBSS and added to the plates. For each compound tested, a duplicate plate was prepared that was not exposed to light as a control for compound toxicity. Plates were then incubated in a dark drawer (for controls), or under UV light (meter reading of 1.6-1.8 mW/cm$^2$) for 50 minutes. Cells were then washed with HBSS, fresh medium was added, and plates were incubated overnight as described above. The following day neutral red was added as an indicator of cell viability. The plates were then incubated for an additional 3 hours. Cells were then washed with HBSS and blotted on absorbent paper to remove excess liquid. A solution of 50% EtOH, 10% glacial acetic acid was added and after 20 minutes incubation, and the plate's absorbance at 535 nm was read using a Wallac Victor 5 spectrophotometer. The phototoxicity reflected the difference between the light-treated and control cultures. The results are given in Table 5. Results for the tetracycline derivative COL-3, as well doxycycline and minocycline are shown for comparison. Compounds which showed phototoxicity are indicated by "**" (e.g., less than 5 µg/mL), compounds which showed moderate phototoxicity are indicated by "*" (e.g., greater than about 5 µg/mL and less than about 25 µg/mL), compounds which showed some phototoxicity are indicated by "**" (e.g., greater than about 25 µg/mL and less than about 75 µg/mL) and compounds that showed minimal or no phototoxicity are indicated by "*" (e.g., greater than about 75 µg/mL).

TABLE 5

| Compound Code | Dark Tox50 (uM) | UV Tox50 (uM) |
|---|---|---|
| Minocycline | * | * |
| Doxycycline | * | *** |
| COL-3 | ** | **** |
| A | * | *** |
| B | * | * |
| C | * | ** |
| D | * | ** |
| E | * | ** |
| F | * | ** |
| G | * | ** |
| H | * | * |
| I | * | * |
| J | * | * |
| K | * | * |
| L | * | **** |
| M | * | * |
| N | * | * |
| O | * | ** |
| P | * | ** |
| Q | * | * |
| R | * | * |
| S | * | ** |
| T | * | * |
| U | * | * |
| V | * | * |
| W | * | ** |
| X | * | *** |
| Y | * | * |
| Z | * | * |
| AA | * | * |
| AB | * | *** |
| AC | * | * |
| AD | * | * |
| AE | * | ** |
| AF | * | * |
| AL | * | *** |
| AM | * | * |
| AN | * | ** |
| AO | * | * |
| AQ | * | ** |
| AR | * | ** |
| AS | * | * |
| AT | * | *** |
| AU | * | * |
| AV | * | * |
| AX | * | * |

Example 5

Half-Life Determination of the Oxidation

In this example, the half-life of minocycline and a tetracycline compound used in the methods of the invention were assessed under oxidative conditions, as described in Nilges, et al. (Nilges M, Enochs W, Swartz H. *J. Org. Chem.* 1991, 56, 5623-30). Not to be limited by theory, it is believed that the tissue staining may be caused oxidative instability. The tetracycline compounds were subjected to accelerated oxidation in a continuous-flow microreactor using a 15 molar excess of sodium periodate at pH 11 and 22° C. Aliquots of each reaction mixture were quenched at various time points with ascorbic acid and the disappearance of each compound was determined by RP-HPLC. Pseudo first-order rate constants and $t_{1/2}$ values were obtained from the plots of log (Ao–At/Ao) versus time, where Ao is the HPLC area determined for each compound at time=0 and At is the HPLC area at time=t. The results indicated that minocycline had a half-life for oxidation of 8.2 seconds, while compound B had a half-life for oxidation of 495 seconds.

Example 6

In Vivo Anti-Bacterial Activity with *S. aureus* Model

In this example, the in vivo anti-bacterial activity of the tetracycline compounds used in the methods of the invention were assessed.

Groups of five mice were injected intraperitoneally with a lethal dose of *S. aureus* RN450 in a medium of mucin. Mice were evaluated at 24 hours to determine survival. Untreated animals experienced 100% mortality. Subcutaneous treatment with a single dose of minocycline, doxycycline or the test compound resulted in 100% survival. In some instances, a dose response study was performed with the compound such that a $PD_{50}$ (a dose of compound that protects 50% of the animals) could be calculated. The results are shown in Table 6.

TABLE 6

| Compound | Dose (mg/kg) | Percent Survival | PD50 (mg/kg) |
| --- | --- | --- | --- |
| Untreated | — | 0(0/5) | — |
| Minocycline | 5 | 100 (5/5) | 0.72 |
| Doxycycline | 5 | 100 (5/5) | 0.13 |
| A | 5 | 100 (5/5) | — |
| C | 5 | 100 (5/5) | |
| P | 5 | 100 (5/5) | 0.13 |
| Q | 5 | 100 (5/5) | 0.45 |
| V | | | 1.4 |
| W | | | 1.08 |
| AA | 5 | 100 (5/5) | — |
| AD | | | 4.54 |
| AN | | | 1.1 |
| AF | | | 0.23 |
| AO | | | 0.48 |
| AR | | 0.58 | 0.58 |
| AT | | | 1.11 |

Example 7

Figure 2:
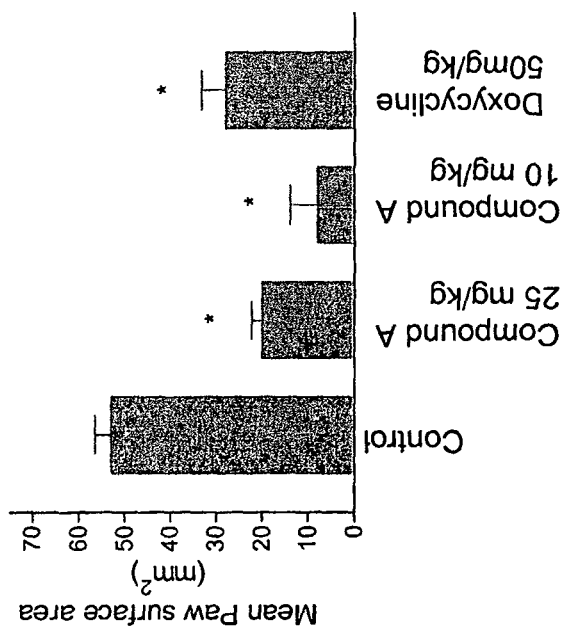
FIG. 2 is a graphical comparison of the modulation of carregeenan induced inflammation in the rat paw edema model between minocycline and compound P.

In Vivo Anti-Inflammatory Activity with Rat Carrageenan-Induced Paw Edema Inflammatory Model To asses the anti-inflammatory potential of the tetracycline compounds used in the methods of the invention, the tetracycline compounds were assessed in a model of carrageenan induced rat paw inflammation. The model used a sub-plantar injection of carrageenan in the rat to induce an inflammatory response. The test compound or saline (control) was administered IP 30 minutes before a subplantar injection of carrageenan (1.5 mg/0.1 mL). Paw volume was measured (mm²) before subplantar injection and again 3 hours after the injection of carrageenan using a plethysmometer. The results are shown in FIGS. 1 and 2. Significant differences as determined by a Kruskal-Wallis One Way ANOVA are noted between the inflammation of the untreated controls versus treated animals (p=0.5)

FIG. 1 compares the modulation of carregeenan induced inflammation of doxycycline with various doses of compound A. Doxycycline exhibited a 50% effective concentration ($EC_{50}$) at approximately 50 mg/kg, while compound A exhibited improved activity.

FIG. 2 compares the modulation of carregeenan induced inflammation of minocycline compared with various doses of compound P. Minocycline exhibited an $EC_{50}$ at approximately 50 mg/kg, while compound P exhibited similar or improved activity.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for treating a subject suffering from acne, comprising administering to the subject an effective amount of a substituted tetracycline compound that is

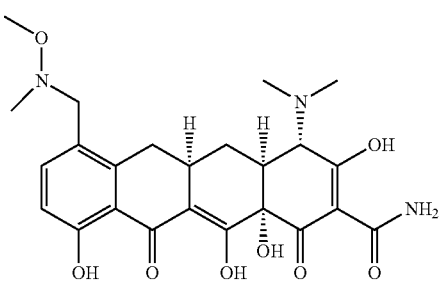 [SMILES: CON(C)Cc1ccc(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

2. A method for treating a subject suffering from rosacea, comprising administering to the subject an effective amount of a substituted tetracycline compound that is

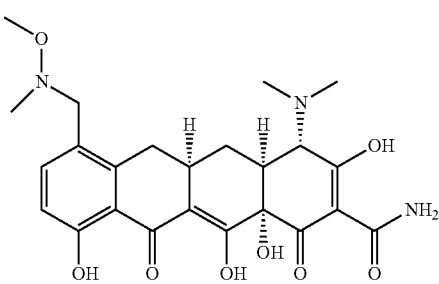 [SMILES: CON(C)Cc1ccc(O)c2c1C[C@H]1C[C@H]3[C@H](N(C)C)C(O)=C(C(N)=O)C(=O)[C@@]3(O)C(O)=C1C2=O]

or a pharmaceutically acceptable salt thereof.

3. The method according to claim 1, wherein the amount of substituted tetracycline compound administered to the subject is in a range of from 0.01 to 100 milligrams per kilogram of body weight of the subject.

4. The method according to claim 2, wherein the amount of substituted tetracycline compound administered to the subject is in a range of from 0.01 to 100 milligrams per kilogram of body weight of the subject.

5. The method according to claim 1, wherein the amount of substituted tetracycline compound administered to the subject is in a range of from 0.1 to 50 milligrams per kilogram of body weight of the subject.

6. The method according to claim 2, wherein the amount of substituted tetracycline compound administered to the subject is in a range of from 0.1 to 50 milligrams per kilogram of body weight of the subject.

7. The method according to claim 1, wherein the amount of substituted tetracycline compound administered to the subject is in a range of from 1 to 20 milligrams per kilogram of body weight of the subject.

8. The method according to claim 2, wherein the amount of substituted tetracycline compound administered to the subject is in a range of from 1 to 20 milligrams per kilogram of body weight of the subject.

9. The method according to claim 1, wherein the subject is a human.

10. The method according to claim 2, wherein the subject is a human.

* * * * *